United States Patent [19]
Benkowski et al.

[11] Patent Number: 5,947,892
[45] Date of Patent: *Sep. 7, 1999

[54] ROTARY BLOOD PUMP

[75] Inventors: Robert J. Benkowski, League City, Tex.; Cetin Kiris; Dochan Kwak, both of Palo Alto, Calif.; Bernard J. Rosenbaum, Seabrook, Tex.; James W. Bacak; Michael E. DeBakey, both of Houston, Tex.

[73] Assignee: MicroMed Technology, Inc., The Woodlands, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/766,886

[22] Filed: Dec. 13, 1996

Related U.S. Application Data

[60] Continuation-in-part of application No. 08/451,709, May 26, 1995, Pat. No. 5,678,306, which is a division of application No. 08/153,595, Nov. 10, 1993, Pat. No. 5,527,159.

[51] Int. Cl.⁶ ..................................................... A61M 1/12
[52] U.S. Cl. .................................. 600/16; 623/3; 415/900
[58] Field of Search ................................. 415/700; 623/3; 600/16–18

[56] References Cited

U.S. PATENT DOCUMENTS

| | | |
|---|---|---|
| 2,274,274 | 2/1942 | Pezzillo . |
| 2,485,408 | 10/1949 | Pezzillo . |
| 2,747,512 | 5/1956 | Fouche . |
| 3,774,243 | 11/1973 | Ng et al. . |
| 3,837,922 | 9/1974 | Ng et al. . |
| 3,911,897 | 10/1975 | Leachman, Jr. . |
| 3,911,898 | 10/1975 | Leachman, Jr. . |
| 4,004,299 | 1/1977 | Runge . |
| 4,135,253 | 1/1979 | Reich et al. . |
| 4,166,466 | 9/1979 | Jarvik . |

(List continued on next page.)

OTHER PUBLICATIONS

Dialog abstract 7383895, Qian, K., "Low Hemolysis Pulsatile Impeller Pump Design Concepts and Experimental Results" (1989).

Dialog abstract 98304, Qian, K. et al, "Development of Pulsatile Implantable Impeller Pump with Low Hemolysis" (1990).

Dialog abstract 6632689, Qian, K. et al, "A New Impeller Blood Pump Design In–Vitro and In–Vivo Studies" (1988).

(List continued on next page.)

*Primary Examiner*—William E. Kamm
*Assistant Examiner*—George R. Evanisko
*Attorney, Agent, or Firm*—Arnold White & Durkee

[57] ABSTRACT

A blood pump that comprises a pump housing having a blood flow path therethrough, a blood inlet, and a blood outlet; a stator mounted to the pump housing, the stator having a stator field winding for producing a stator magnetic field; a flow straightener located within the pump housing, and comprising a flow straightener hub and at least one flow straightener blade attached to the flow straightener hub; a rotor mounted within the pump housing for rotation in response to the stator magnetic field, the rotor comprising an inducer and an impeller; the inducer being located downstream of the flow straightener, and comprising an inducer hub and at least one inducer blade attached to the inducer hub; the impeller being located downstream of the inducer, and comprising an impeller hub and at least one impeller blade attached to the impeller hub; and preferably also comprising a diffuser downstream of the impeller, the diffuser comprising a diffuser hub and at least one diffuser blade. Blood flow stagnation and clot formation within the pump are minimized by, among other things, providing the inducer hub with a diameter greater than the diameter of the flow straightener hub; by optimizing the axial spacing between the flow straightener hub and the inducer hub, and between the impeller hub and the diffuser hub; by optimizing the inlet angle of the diffuser blades; and by providing fillets or curved transitions between the upstream end of the inducer hub and the shaft mounted therein, and between the impeller hub and the shaft mounted therein.

39 Claims, 13 Drawing Sheets

U.S. PATENT DOCUMENTS

| | | |
|---|---|---|
| 4,169,990 | 10/1979 | Lerdman . |
| 4,173,796 | 11/1979 | Jarvik . |
| 4,302,854 | 12/1981 | Runge . |
| 4,382,199 | 5/1983 | Isaacson . |
| 4,397,049 | 8/1983 | Robinson et al. . |
| 4,403,177 | 9/1983 | Weber et al. . |
| 4,507,048 | 3/1985 | Belenger et al. . |
| 4,546,293 | 10/1985 | Peterson et al. . |
| 4,583,523 | 4/1986 | Kleinke et al. . |
| 4,597,767 | 7/1986 | Lenkei . |
| 4,611,578 | 9/1986 | Heimes . |
| 4,625,712 | 12/1986 | Wampler . |
| 4,662,358 | 5/1987 | Farrar et al. . |
| 4,665,896 | 5/1987 | LaForge et al. . |
| 4,687,424 | 8/1987 | Heimes . |
| 4,688,998 | 8/1987 | Olsen et al. . |
| 4,704,121 | 11/1987 | Moise . |
| 4,712,648 | 12/1987 | Mattes et al. . |
| 4,718,903 | 1/1988 | Min et al. . |
| 4,750,903 | 6/1988 | Cheng . |
| 4,763,032 | 8/1988 | Bramm et al. . |
| 4,779,614 | 10/1988 | Moise . |
| 4,817,586 | 4/1989 | Wampler . |
| 4,846,152 | 7/1989 | Wampler et al. . |
| 4,863,461 | 9/1989 | Jarvik . |
| 4,895,557 | 1/1990 | Moise et al. . |
| 4,906,229 | 3/1990 | Wampler . |
| 4,908,012 | 3/1990 | Moise et al. . |
| 4,944,722 | 7/1990 | Carriker et al. . |
| 4,944,748 | 7/1990 | Bramm et al. . |
| 4,957,504 | 9/1990 | Chardack . |
| 4,964,864 | 10/1990 | Summers et al. . |
| 4,984,972 | 1/1991 | Clausen et al. . |
| 4,994,078 | 2/1991 | Jarvik . |
| 5,007,927 | 4/1991 | Badylak et al. . |
| 5,040,944 | 8/1991 | Cook . |
| 5,049,134 | 9/1991 | Golding et al. . |
| 5,055,005 | 10/1991 | Kletschka . |
| 5,092,879 | 3/1992 | Jarvik . |
| 5,112,292 | 5/1992 | Hwang et al. . |
| 5,112,349 | 5/1992 | Summers et al. . |
| 5,135,483 | 8/1992 | Wagner et al. . |
| 5,174,726 | 12/1992 | Findlay . |
| 5,205,721 | 4/1993 | Isaacson . |
| 5,209,650 | 5/1993 | Lemieux . |
| 5,211,546 | 5/1993 | Isaacson et al. . |
| 5,258,696 | 11/1993 | Le . |
| 5,269,811 | 12/1993 | Hayes et al. . |
| 5,275,580 | 1/1994 | Yamazaki ................................. 623/3 |
| 5,290,227 | 3/1994 | Pasque . |
| 5,321,342 | 6/1994 | Kruse . |
| 5,360,317 | 11/1994 | Clausen et al. . |
| 5,368,438 | 11/1994 | Raible . |
| 5,370,509 | 12/1994 | Golding et al. . |
| 5,376,114 | 12/1994 | Jarvik . |
| 5,486,286 | 1/1996 | Peterson et al. . |
| 5,507,629 | 4/1996 | Jarvik . |
| 5,527,159 | 6/1996 | Bozeman et al. . |
| 5,603,337 | 2/1997 | Jarvik . |
| 5,613,935 | 3/1997 | Jarvik . |

OTHER PUBLICATIONS

Kiris et al., "Computational Flow Analysis of Left Ventricular Assist Device," pp. 1–6.

Aber et al., "Development of the NASA/Baylor VAD," NASA, Washington, Technology 2003: The Fourth National Technology Transfer Conference and Exposition, vol. 1, pp. 151–157 (Feb. 1, 1994) (also presented at Fourth National Technology Transfer Conference and Exposition, Dec. 7–9, 1993, Anaheim, CA).

Bernard et al., "An investigation of induced chronic hyperthermia and in vivo heat dissipation," The Journal of Thoracic and Cardiovascular Surgery, vol. 52, No. 5, pp. 611–617 (Nov. 1966).

Van Citters et al., "Artificial Heart and Assist Devices: Directions, Needs, Costs, Societal and Ethical Issues," Artificial Organs, vol. 9, No. 4, pp. 375–415 (1985).

Rintoul et al, "An Intrathoracic Left Ventricular Assist System: Utilization of Results from a Development Program", ASAIO Transactions, vol. 36, No. 3, pp. M392–M395 (Jul.–Sep. 1990).

Nosé, "Intrathoracic Cardiac Prosthesis: Is it Really Not Clinically Acceptable?," Artificial Organs, vol. 15, No. 3, pp. 161–163 (Jun. 1991).

Shiono et al., "Ventricular assist device as a mechanical support for postcardiotomy failure and as a bridge to heart transplantation," Cardio–thoracic surgery, Minami et al. (eds.), Elsevier Science Publishers B.V., pp. 197–204 (Sep. 1991).

Nosé, "Is a Pulsatile Cardiac Prosthesis a Dying Dinosaur?," Artificial Organs, vol. 16, No. 3, pp. 233–234 (Jun. 1992).

Butler et al., "Development of an Axial Flow Blood Pump LVAS," ASAIO Journal, pp. M296–M300 (1992).

Nosé, "Is A Totally Implantable Artificial Heart Realistic?," Artificial Organs, vol. 16, No. 1, pp. 19–42 (1992).

Treichler et al., "A Fluid Dynamic Analysis of a Rotary Blood Pump for Design Improvement," Artificial Organs, vol. 17, No. 9, pp. 797–808 (Sep. 1993).

Nosé, "Nonpulsatile Mode of Blood Flow Required for Cardiopulmonary Bypass and Total Body Perfusion," Artificial Organs, vol. 17, No. 2, pp. 92–102 (1993).

Wampler et al., "A Second Generation Intraarterial Ventricular Assist Device," ASAIO Journal, pp. M218–M223 (1993).

Yamazaki et al., "Development of a Miniature Intraventricular Axial Flow Blood Pump," ASAIO Journal, pp. M224–M230 (1993).

Antaki et al., "In Vivo Evaluation of the Nimbus Axial Flow Ventricular Assist System," ASAIO Journal, pp. M231–M236 (1993).

Damm et al., "In Vitro Performance of the Baylor/NASA Axial Flow Pump," Artificial Organs, vol. 17, No. 7 (Jul. 1993).

Macris et al., "In Vivo Evaluation of an Intraventricular Electric Axial Flow Pump for Left Ventricular Assistance," ASAIO Journal, 40(3):M719–M722 (Jul.–Sep. 1994).

Damm et al., "Axial Flow Ventricular Assist Device: System Performance Considerations," Artificial Organs, vol. 18, No. 1, pp. 44–48 (Jan. 1994).

Mizuguchi et al., "Development of the Baylor/NASA Axial Flow Ventricular Assist Device: In Vitro Performance and Systematic Hemolysis Test Results," Artificial Organs, vol. 18, No. 1, pp. 32–43 (Jan. 1994).

Konishi et al., "Dynamic Systemic Vascular Resistance in a Sheep Supported with a Nimbus AxiPump," ASAIO Journal, pp. M299–M302 (1994).

Mizuguchi et al., "Does Hematocrit Affect In Vitro Hemolysis Test Results? Preliminary Study with Baylor/NASA Prototype Axial Flow Pump," Artificial Organs, vol. 18, No. 9, pp. 650–656 (1994).

Wanke, "The Problem of Vibrations on the Baylor/NASA Implantable Axial Flow Pump in the Viewpoint of Bearing Lifetime and Pump Performance," Baylor College of Medicine, pp. 1–55 (Apr. 1994).

Mizuguchi et al., "Development of Axial Flow Ventricular Assist Device: In Vitro and In Vivo Evaluation," Artificial Organs, vol. 19, No. 7, pp. 653–659 (Jul. 1995).

Jarvik, "System Considerations Favoring Rotary Artificial Hearts with Blood–Immersed Bearings," Artificial Organs, vol. 19, No. 7, pp. 565–570 (1995).

Wernicke et al., "A Fluid Dynamic Analysis Using Flow Visualization of the Baylor/NASA Implantable Axial Flow Blood Pump for Design Improvement," Artificial Organs, vol. 19, No. 2, pp. 161–177 (1995).

Suraj, "Flow Studies of an Axial Left Ventricular Assist Pump," pp. 1–32 (Mar. 1995).

Mizuguchi et al., "In Vitro Hemolysis Test Method for Developing an Axial Flow Ventricular Assist Device," Artificial Heart, 5th Edit., Springer–Verlag, pp. 237–244 (1996).

Ohtsubo, "Summary of the Third Congress of the International Society for Rotary Blood Pumps, Houston, Texas, U.S.A., 1995," Artificial Organs, vol. 20, No. 6, pp. 737–738 (1996).

Kawahito et al., "Ex Vivo Evaluation of the NASA/DeBakey Axial Flow Ventricular Assist Device," ASAIO Journal, vol. 42, No. 5, pp. M754–M757 (Sep.–Oct. 1996).

Kawahito et al., "Ex Vivo Phase I Evaluation of the DeBakey/NASA Axial Flow Ventricular Assist Device," Artificial Organs, vol. 20, No. 1, pp. 47–52 (1996).

Benkowski et al., "Development of a VAD Using Computer Aided Design, Manufacturing and Engineering," ASAIO Journal, vol. 42, No. 2, p. 57 and Abstract (Mar.–Apr. 1996) (also presented at the Cardiovascular Science and Technology Conference, May 2–4,1996, Washington, D.C.).

Kawahito et al., "Improved Flow Straighteners Reduce Thrombus in the NASA/DeBakey Axial Flow Ventricular Assist Device," Artificial Organs, vol. 21, No. 4, pp. 339–343 (Apr. 1997).

Henig, R.M., "Tiny Pump Gives Heart a Big Rest", Health—The Washington Post, A Weekly Journal of Medicine, Science and Society, Jan. 31, 1989.

Orth, J.L. et al, "An Electronically Commutated Brushless DC Motor Applied to a Total Artificial Heart", Proceedings of the First Annual International Motorcon '81 Conference, Chicago, IL, 667–676 (Jun. 1981).

Mizuguchi, K. et al, "Does Hematocrit Affect In Vitro Hemolysis Test Results? Preliminary Study with Baylor/NASA Prototype Axial Flow Pump", Artificial Organs, 18(9):650–656 (1994).

Damm, G. et al, "Axial Flow Ventricular Assist Device: System Performance Considerations", Artificial Organs, 18(1):44–48 (1993).

Jarvik, Robert, "System Considerations Favoring Rotary Artificial Hearts with Blood–Immersed Bearings", Artificial Organs, 19(7):565–570 (1995).

Damm, G. et al, "In Vitro Performance of the Baylor/NASA Axial Flow Pump", Artificial Organs, 17(7):609–613 (1993).

Mizuguchi, K. et al, "Development of the Baylor/NASA Axial Flow Ventricular Assist Device: In Vitro Performance and Systematic Hemolysis Test Results", Artificial Organs, 18(1):32–43 (1994).

Mizuguchi, K. et al, "Development of an Axial Flow Ventricular Assist Device: In Vitro and In Vivo Evaluation", Artificial Organs, 19(7):653–659 (1995).

Macris, M.P. et al, "In Vivo Evaluation of an Intraventricular Electric Axial Flow Pump for Left Ventricular Assistance", ASAIO Journal, Slide Forum–CVS 8, M719–M722 (1992).

Wernicke, J.T. et al, "A Fluid Dynamic Analysis Using Flow Visualization of the Baylor/NASA Implantable Axial Flow Blood Pump for Design Improvement", Artificial Organs, 19(2):161–177 (1995).

Mizuguchi, K. et al, "Development of the Baylor/NASA Axial Flow Pump", Artificial Organs, 17(6) (1993).

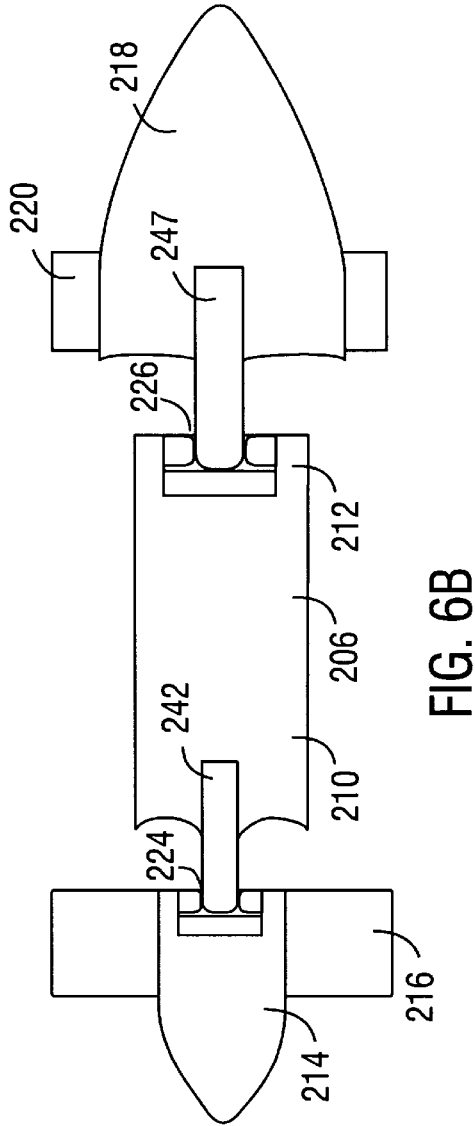
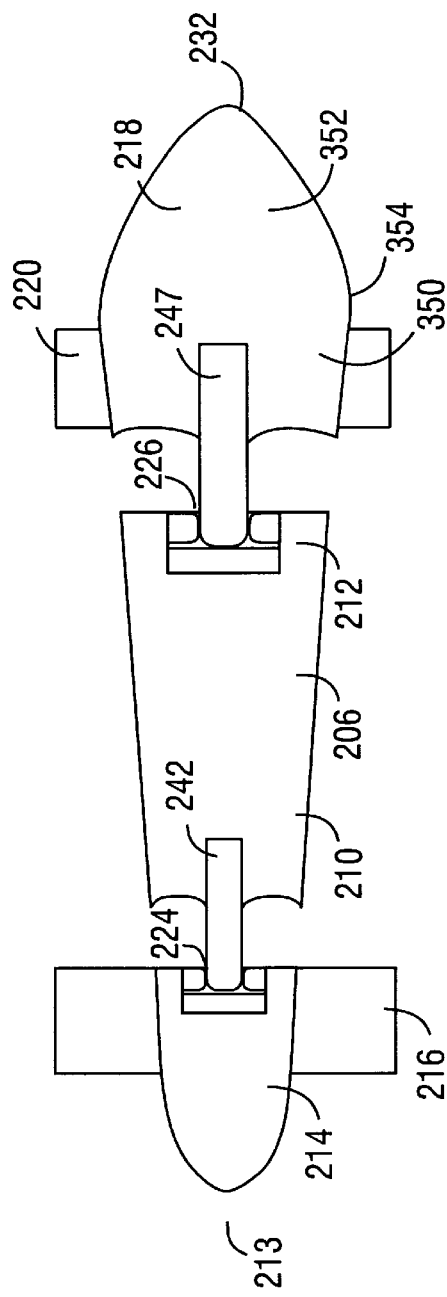

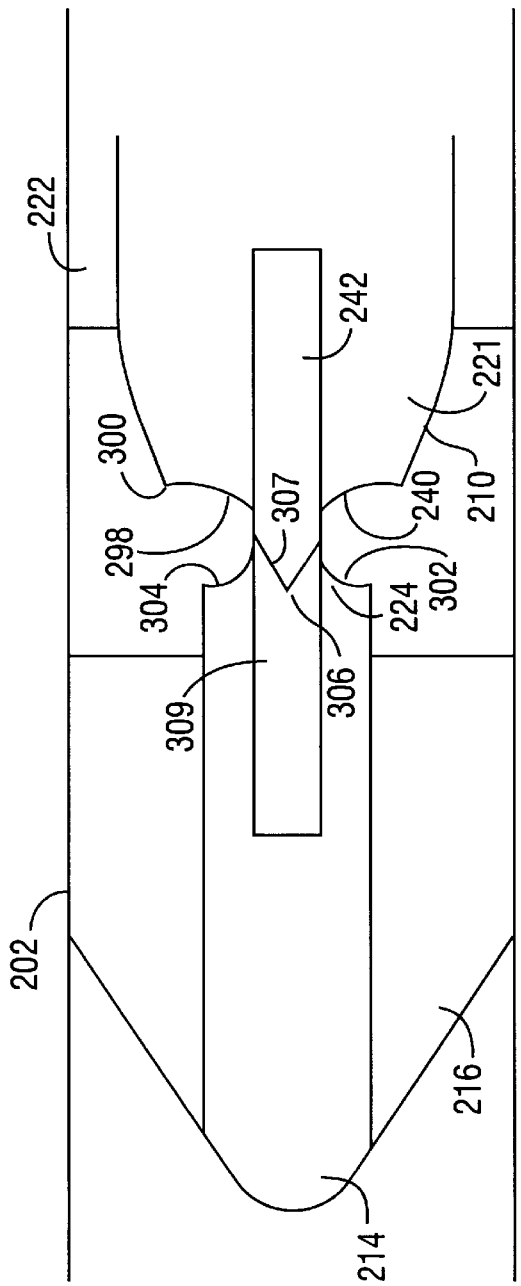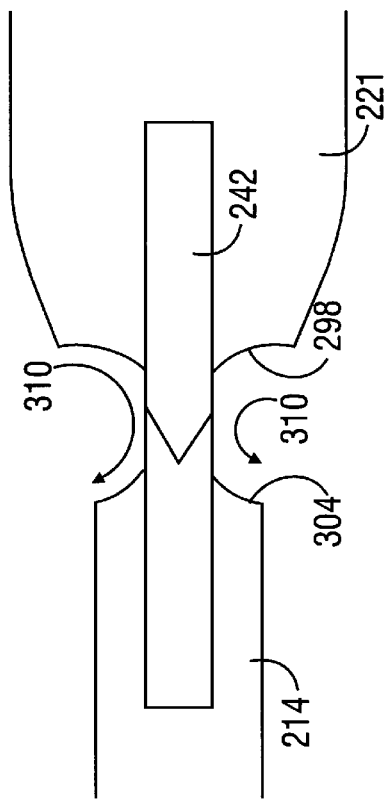

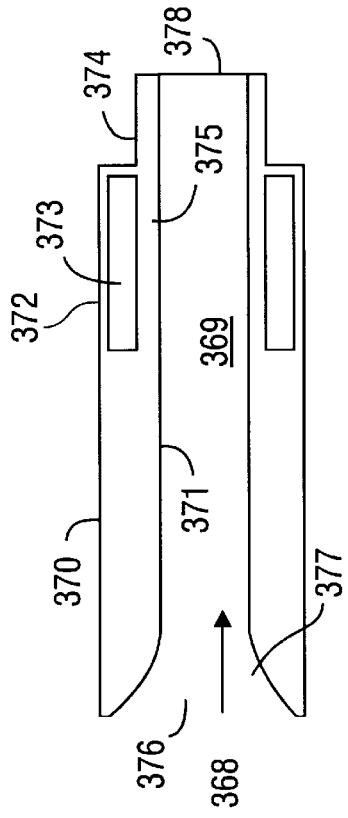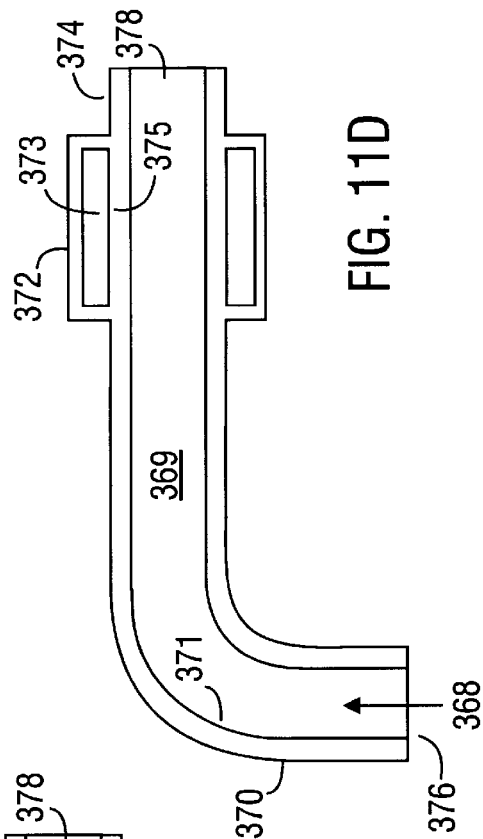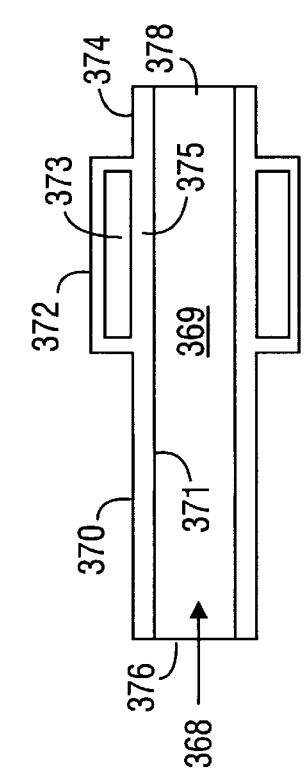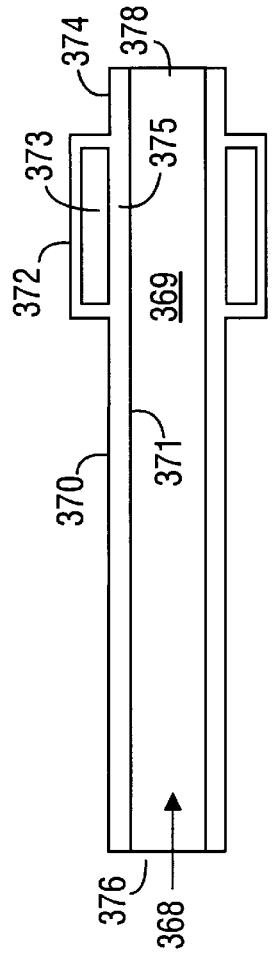
FIG. 11A
FIG. 11B
FIG. 11C
FIG. 11D

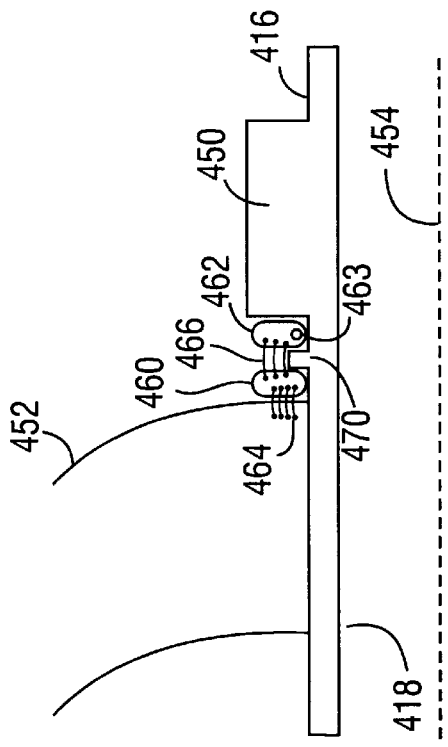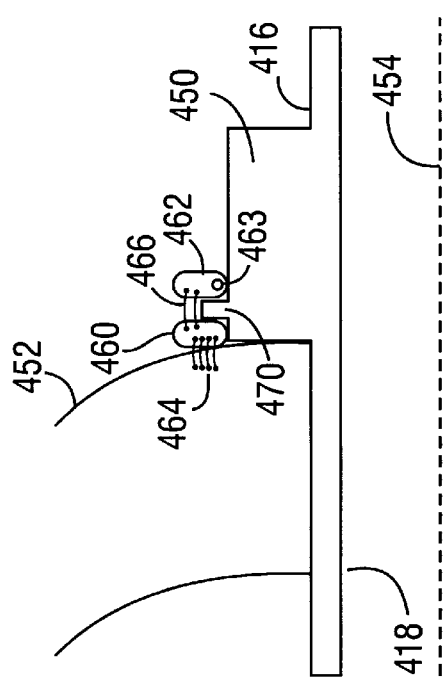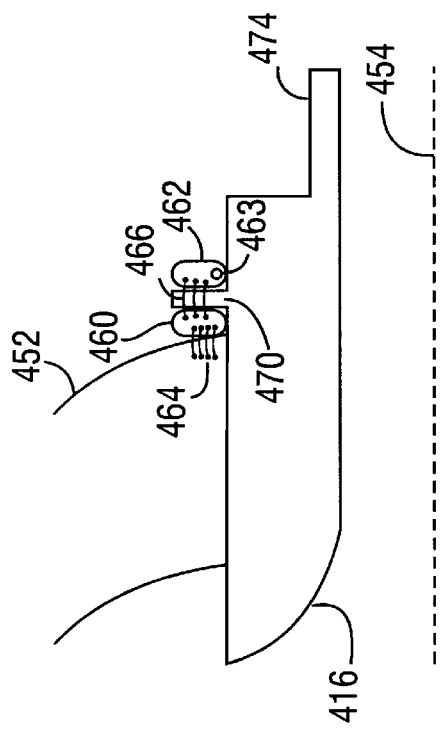

ROTARY BLOOD PUMP

This application is a continuation-in-part of U.S. application Ser. No. 08/451,709, filed on May 26, 1995, now U.S. Pat. No. 5,678,306 which was a divisional of U.S. application Ser. No. 08/153,595, filed on Nov. 10, 1993, now issued as U.S. Pat. No. 5,527,159.

The invention described herein was made in the performance of work under a NASA funding agreement and by an employee of the United States Government, and it may be manufactured and used by or for the Government for governmental purposes without the payment of any royalties thereon or therefore.

BACKGROUND OF THE INVENTION

The present invention relates to an axial-flow rotary blood pump that can be implanted into the chest of a human and can be used to assist a human heart in pumping blood.

One application of blood pumps is to boost blood circulation in patients whose heart still functions but is not pumping blood at an adequate rate. The estimated need for a relatively simple, long-term ventricle assist device (VAD) is presently projected at between 50,000 and 100,000 patients per year in the United States alone.

Despite this need, prior pumps have not been entirely satisfactory due to a variety of problems. For example, fluid dynamic forces in the pump may activate platelets, leading to formation of blood clots. High shear stresses in the pump may damage red blood cells. These problems can be exacerbated by the small size required for a blood pump to be implantable, which necessitates a high rotational speed in a rotary type pump. Further, some prior devices have required large external support equipment, resulting in little or no patient mobility.

Problems of prior pumps that have limited their clinical use to relatively short times include the following: (1) blood damage which may occur when blood comes into contact with rotor bearings, (2) the need for bearing purge systems which may require percutaneous (through the skin) saline solution pump systems, (3) bearing seizure resulting from the considerable thrust and torque loads, or from dried blood sticking on the bearing surfaces, (4) problems of blood damage (hemolysis) and blood clotting (thrombosis) caused by relative rotational movement of the components of the pump, (5) pump and control size and shape limitations necessary for implantation or convenient mobility, (6) weight limitations for implantation to avoid tearing of implant grafts due to inertia of sudden movement, (7) difficulty in coordinating and optimizing the many pump design parameters which may affect hemolysis, (8) high power consumption that requires a larger power supply, (9) motor inefficiency caused by a large air gap between motor windings and drive magnets, (10) heat flow from the device to the body, (11) complex Hall Effect sensors/electronics for rotary control, (12) the substantial desire for minimizing percutaneous (through the skin) insertions, including support lines and tubes, (13) large pump and related hose internal volume which may cause an initial shock when filled with saline solution while starting the pump, and (14) high cost effectively makes the device unavailable for many patients who could otherwise benefit from it.

Although significant efforts have been made to solving the problems associated with implantable blood pumps, there is still a great need for an improved pump that can be used for an extended period in a human as a ventricle assist device, and that is reliable, compact, relatively inexpensive, requires limited percutaneous insertions, and produces fewer blood clots and less blood damage problems.

SUMMARY OF THE INVENTION

The present invention concerns a blood pump that includes a pump housing, a stator, a rotor, a diffuser, and preferably also includes a flow straightener. The housing includes a flow tube having a blood flow path therethrough, a blood inlet, and a blood outlet. The stator is attached to the pump housing, is preferably located outside the flow tube, and has a stator field winding for producing a stator magnetic field. The flow straightener is located within the flow tube, and includes a flow straightener hub and at least one flow straightener blade attached to the flow straightener hub. The rotor is located within the flow tube for rotation in response to the stator magnetic field, and includes an inducer and an impeller. The inducer is located downstream of the flow straightener, and includes an inducer hub and at least one inducer blade attached to the inducer hub. The impeller is located downstream of the inducer, and includes an impeller hub and at least one impeller blade attached to the impeller hub. The diffuser is located within the flow tube downstream of the impeller, and includes a diffuser hub and at least one diffuser blade attached to the diffuser hub. The inducer hub has an upstream end and the flow straightener hub has a downstream end, and the upstream end of the inducer hub has a diameter greater than the diameter of the downstream end of the flow straightener hub. The upstream end of the diffuser hub preferably has a diameter greater than the diameter of the downstream end of the impeller hub.

There is an axial gap between the downstream end of the flow straightener hub and the upstream end of the inducer hub, and the size of that gap preferably is selected to induce a single blood recirculation flow pattern in the gap. Likewise, there is an axial gap between the downstream end of the impeller hub and the upstream end of the diffuser hub, and the size of the gap is preferably sized so as to induce a single blood recirculation flow pattern in the gap. In a preferred embodiment, the flow straightener hub is axially spaced from the inducer hub by between about 0.05 and about 0.09 inches, and the impeller hub is axially spaced from the diffuser hub by between about 0.05 and about 0.09 inches.

In one embodiment, the pump includes a front bearing assembly which comprises a front shaft and a bearing, with one of the front shaft and bearing being attached to the upstream end of the inducer hub, and the other being attached to the downstream end of the flow straightener hub. Most preferably, the front shaft is attached to the upstream end of the inducer hub, and there is a curved transition between the upstream end of the inducer hub and the front shaft.

In an alternate embodiment, the front shaft has two interacting parts, one which has an end connected to the flow straightener hub, and other having an end connected to the inducer hub. The two interacting parts of the front shaft can suitably form a needle bearing.

The pump can also include a rear bearing assembly which comprises a rear shaft and a bearing, with one of the rear shaft and bearing being attached to the downstream end of the impeller hub, and the other being attached to the upstream end of the diffuser hub. Most preferably, the rear shaft is attached to the downstream end of the impeller hub, and there is a curved transition between the downstream end of the impeller hub and the rear shaft.

The inducer, the impeller, and the diffuser preferably all have a common longitudinal axis, and in embodiments of the pump that include a flow straightener, it will preferably also have the same common longitudinal axis.

In various embodiments of the pump, the diameter of the inducer hub can increase from its upstream end to its downstream end; the impeller hub can have a diameter no less than the diameter of the inducer hub; and/or the diameter of the flow straightener hub, inducer hub, and the impeller hub can each increase from their upstream end to their downstream end. In one particular embodiment of the pump, the diffuser hub comprises an upstream segment and a downstream segment, both segments being integral parts of the diffuser hub, and an apex at the outer diameter of the diffuser hub at the point where the upstream segment meets the downstream segment. The diameter of upstream segment increases from its upstream end to the apex, and the diameter of the downstream segment decreases from the apex to its downstream end.

Each diffuser blade preferably has an inlet angle between about 25°–35°. In addition, the pump preferably has at least one interconnecting blade segment which interconnects at least one inducer blade and at least one impeller blade to form a single continuous blade through the inducer and the impeller of the rotor.

The outer surface of the pump housing can have different configurations. For example, the pump housing's outer surface will typically include an inlet housing segment, a stator housing segment, and an outlet housing segment. The stator housing segment can have a larger outer diameter than the inlet housing segment and the outlet housing segment. Alternatively, the inlet housing segment and the stator housing segment can have substantially the same outer diameter, and the outlet housing segment can have a smaller outer diameter. The inlet housing segment can be straight or curved.

One embodiment of the pump also includes structure for attaching a vascular outflow graft to the outlet of the pump. In one such version, the downstream end of the outlet housing segment has a tapered thickness, with the thickness being its minimum at the outlet end of the housing. The pump can include a retaining member disposed around the outer diameter of the outlet housing segment, adapted to hold an outflow graft on the outlet housing segment. The retaining member preferably has a tapered thickness along its axial length. A segment of the outflow graft is compressed between the retaining member and the outlet housing segment, and the compressed segment of the outflow graft has an upstream end and a downstream end. The retaining member has a different angle of taper than the angle of taper for the downstream end of the outlet housing segment, whereby the compressed segment of the outflow graft is compressed to a greater extent at its upstream end than at its downstream end.

The present invention also concerns a blood pump implant assembly that includes a blood pump as described above, and further comprising at least one sewing ring which is attached to the housing of the blood pump, and sutures attaching the sewing ring to the outer wall of the heart of a human patient. Depending on the pump configuration employed, the inlet housing segment of the pump can be inserted into the heart's left ventricle without passing through any other chamber of the heart, or, alternatively, the inlet housing segment can be inserted into the left atrium of the heart, through the mitral valve, and into the left ventricle. To facilitate different means of implantation into the heart, the inlet housing segment can be curved or straight, and can be attached to a curved inlet cannula, a straight inlet cannula, or a flexible inlet cannula.

The present invention provides a number of advantages for the construction and use of blood pumps, especially for clinical use implanted in humans. It provides an axial flow ventricle assist device which can be implanted in a human and used to increase the rate of blood pumped to the body's tissues for an extended period of time. Internal configuration of the blood pump of the present invention promotes desirable continuous blood circulation patterns within the pump, and minimizes blood stagnation within the pump and clot formation. The stepped hub diameters, optimized axial distance of the front and rear hub gaps, and appropriately curved surfaces between the upstream face of the inducer hub and the front shaft, and between the downstream face of the impeller hub and the rear shaft, contribute to this advantage. In order to be able to incorporate dished faces and/or fillets on the faces of the respective hubs, it is advantageous for the front bearing assembly to include a shaft fixedly mounted on the inducer and a bearing mounted on the flow straightener hub, and for the rear bearing assembly to include a shaft fixedly mounted on the impeller and a bearing mounted on the diffuser hub.

BRIEF DESCRIPTION OF THE DRAWINGS

FIG. 6B is an elevational view, partly in section, of internals of a rotary blood pump in accordance with the present invention;

FIG. 6C is an elevational view, partly in section, of internals of another embodiment of a rotary blood pump in accordance with the present invention;

FIG. 7 is a partial elevational view, partly in section, of the upstream end of the internals of a rotary blood pump in accordance with the present invention;

FIG. 8 is a partial elevational view of the upstream end of the internals of another embodiment of a rotary blood pump in accordance with the present invention;

FIGS. 11A, 11B, 11C, and 11D are elevational view in section of the housings of different embodiments of blood pumps in accordance with the present invention.

FIG. 13 is an elevational view in section of a portion of a blood pump attached to a heart in accordance with the present invention;

FIG. 14 is an elevational view in section of another embodiment of a portion of a blood pump attached to a heart in accordance with the present invention;

FIG. 15 is an elevational view in section of another embodiment of a portion of a blood pump attached to a heart in accordance with the present invention;

DESCRIPTION OF SPECIFIC EMBODIMENTS

A rotary blood pump is disclosed in U.S. Pat. No. 5,527,159. That patent is incorporated here by reference. The present invention provides further improvements to the pump.

Figure 1:
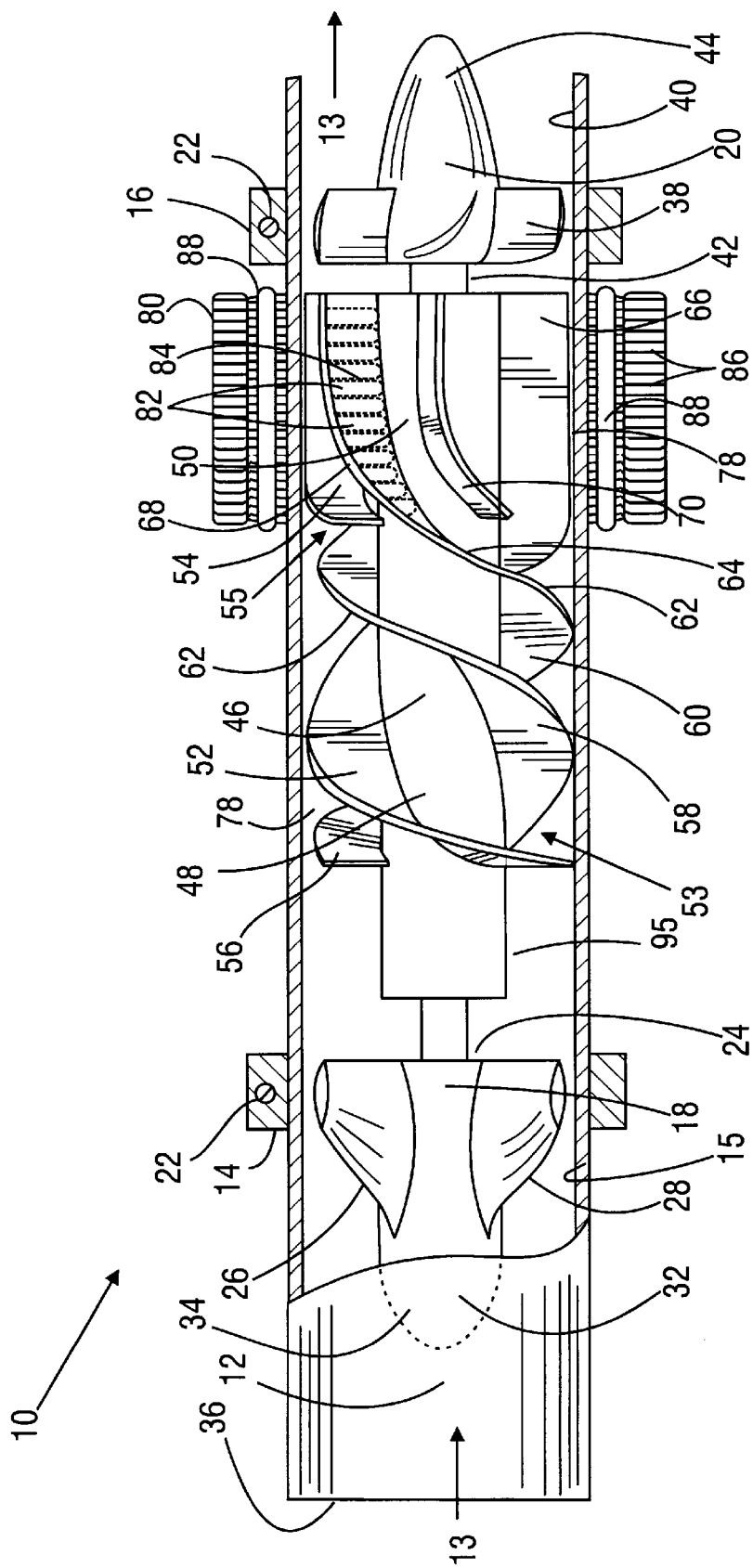
FIG. 1 is an elevational view, partially in section, of a rotary blood pump, with blood flow generally from left to right.

FIG. 1 shows a rotary blood pump 10. The pump 10 includes a preferably metallic tubular pump housing 12 which is, in a preferred embodiment, a straight-sided cylinder. Pump housing 12 has a smooth inner bore wall 15 to minimize thrombus formation. Pump housing 12 defines a blood flow path 13 therethrough in the direction indicated by blood flow arrows shown in FIG. 1.

In the embodiment of FIG. 1, front and rear clamps 14 and 16, respectively, are used to secure flow straightener 18 and diffuser 20 within pump housing 12. Pump housing 12 is sufficiently thin-walled so that the tightening of clamps 14 and 16 with clamp screws 22 locally deforms pump housing 12 about flow straightener 18 and diffuser 20 to affix these components in position. The clamps provide a very convenient means of securing the rotor assembly. Alternatively, other means for securing these components could be used, such as spot welding and fasteners. The presently preferred means of securing the flow straightener 18 and the diffuser 20 to the housing 12 is by interference fit, as will be described in more detail below with respect to FIG. 6A.

Flow straightener 18 can serve two basic functions: (1) it can straighten blood flow to reduce hemolysis while improving pump efficiency, and (2) it can provide a support structure for front bearing assembly 24. It has been found, however, that straightening the blood flow is not desirable, and thus it is preferred to design the blades on the flow straightener 18 so that they support and secure the device, but make little or no change in the direction of blood flow.

Figure 3:
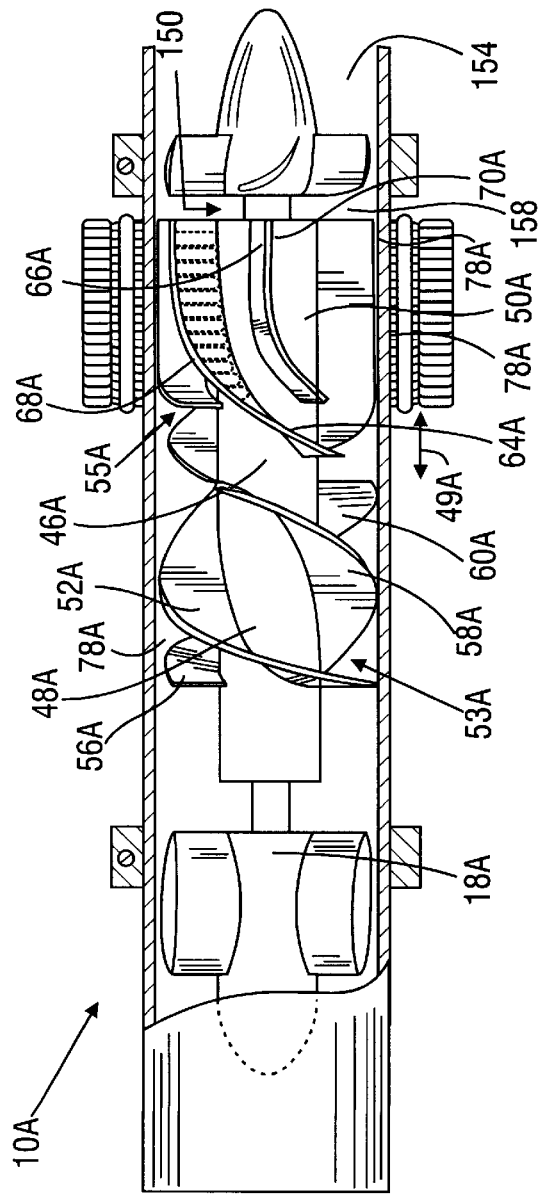
FIG. 3 is an elevational view, partially in section, of an alternative embodiment rotary blood pump having distinct impeller and inducer blades.

Flow straightener 18 preferably has four fixed blades 26, but could have only two blades. Too many blades impede blood flow, while too few blades do not adequately support the front bearing. For purposes of lowering thrombosis, the front edge 28 of each blade 26 is sloped from inner housing wall 15 to flow straightener hub 32 so that blood stagnation caused by contact with blades 26 is minimized. Also to reduce blood trauma, flow straightener hub 32 can be cylindrical with a leading surface 34 that is round or hyperbolic, for example. An alternative embodiment of flow straightener 18a is shown in FIG. 3, and does not have the sloping front edge blades.

The preferred angle of attack of blades 26 is 90°, i.e., the blades would intersect a plane transverse to cylindrical housing 12 at an angle of 90°. This reference for the angle of attack or pitch of the blades will be used throughout this specification.

Flow straightener 18 is preferably metallic, but may also be formed of plastic. If formed of plastic and secured in place by clamp 14, it is necessary to reinforce flow straightener 18 with, for instance, metallic supports to prevent plastic creep deformation. The plastic creep deformation phenomena might otherwise eventually cause flow straightener 18 to come loose from clamp 14. Reinforcement is also necessary with respect to other clamped plastic pump components. However, as mentioned above, the presently preferred embodiment does not use clamps to secure the flow straightener.

Diffuser 20 has two basic purposes: (1) it de-accelerates and redirects the outflow at blood flow path exit 40 axially to boost pump performance, and (2) it serves as a support structure for the rear rotor bearing 42. Diffuser 20 preferably has from 5 to 8 fixed blades 38, with 6 blades being presently preferred. In the embodiment of FIG. 1, blades 38 are fixably engaged with pump housing 12 after rear clamp 16 is tightened by screw 22. However, as with the securing of the flow straightener 18 to the housing 12, the blades 38 of the diffuser 20 are preferably secured to the housing by an interference fit rather than a clamp. This will be discussed in more detail below with respect to FIG. 6A.

To perform the function of de-acceleration and axial redirection of blood flow, each diffuser blade 38 has an entrance angle of from about 10° to 35° for slowing the blood down, and an outlet angle of from about 80° to 90° for redirecting blood flow in an axial direction. Tail cone 44 of diffuser 20 is hyperbolic or generally bullet-shaped to reduce turbulence or wake of blood flow from pump 10 so as to minimize blood damage from such turbulence. Increasing the number of fixed blades tends to decrease hemolysis.

Rotor 46 is supported for rotary movement with pump housing 12 by front and rear bearings 24 and 42, respectively. Rotor 46 is divided into two portions along its axis based on the type and function of the blades disposed thereon. Inducer portion 48 is disposed in the front part of rotor 46, i.e., nearer to the pump inlet 36. Impeller portion 50 is disposed in the rear part of rotor 46 closer to pump outlet 40. It has been found that including an inducer portion that is continuous with the impeller portion in an axial flow pump significantly reduces hemolysis.

It has also been found useful to have a hub extension 95 on the upstream end of the inducer portion 48 (i.e., a hub end portion that does not have any blades on it).

FIG. 3 shows an alternative embodiment pump of the present invention which provides for two distinct sets of axially spaced blades which more clearly distinguish the inducer portion of the rotor from the impeller portion of the rotor. Corresponding components of pump 10 in FIG. 1 and 10a in FIG. 3 are given the same number, with the difference of an "a" suffix to distinguish the components for comparison purposes as necessary. A reference to one number is therefore a reference to its corresponding number in this specification, unless otherwise stated. Where components are substantially different between the two pump versions, completely new numbers are assigned. In pump 10a, inducer portion 48a is separated from impeller portion 50a of rotor 46a by gap 49a, which is preferably less than 0.10 inches. Inducer blade 52a may be tapered (not shown) at forward end 56a so that blade 52a has a smaller radial length at forward end 56a, perhaps even blending into hub 73. However, using the method of the present invention, it has been found that a continuous blade pump has even more reduced levels of hemolysis than the non-continuous blade pump 10a.

Inducer blades 52 are located on inducer portion 48 and impeller blades 54 are located on impeller portion 55. Inducer blades 52 on inducer 53 have a variable pitch along their axial length. It was found that the inducer portion 48 reduced hemolysis by approximately 45% from a pump design without the inducer. Hydraulic efficiency was also increased as the rotation speed required to pump 5 liters/min of blood at 100 mm Hg. dropped from 12,600 rpm to 10,800 rpm. The inducer blades 52 pre-rotate the blood before it enters the main pumping or impeller 54 to reduce hemolysis.

Inducer blades 52 also achieve a pumping action that effectively produces a two-stage, increased efficiency pump. The inducer blade 52 has a leading end 56 and a tailing end 60. A shallow entrance angle effectively engages the blood for movement without damaging the blood. The pitch of inducer blade 52 continues to change along its axial length. It is desired that inducer blades have a wrap around rotor 46. The preferred angles and wrap are described below in Table 1.

The embodiment of pump 10 shown in FIG. 1 includes an interconnecting blade portion 62 which is not included in the embodiment of pump 10a shown in FIG. 3. Although the two-stage pump 10a produces significantly reduced hemolysis and efficient pump operation compared to a single stage pump, it has been discovered that by interconnecting inducer blades 52 with impeller blades 54 with interconnecting blade portion 62, hemolysis is reduced to even lower levels while maintaining efficient pump operation.

Figure 18B:
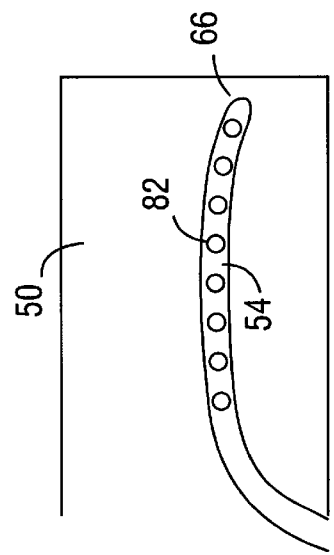
FIGS. 18A and 18B are elevational views of two embodiments of impellers in accordance with the present invention.
Figure 18A:
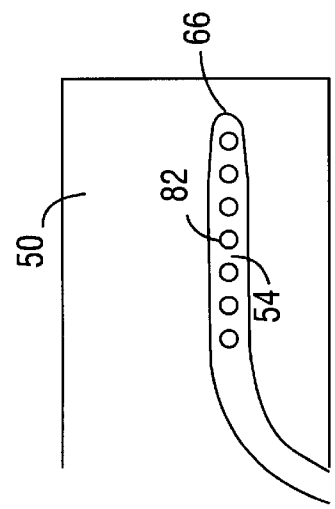

Impeller blades 54 on impeller 55 have an entrance angle in leading end region 64 This may be seen more clearly in FIG. 3, which has no interconnecting blade portion 62. The entrance angle can smoothly taper to an outlet angle of, for example, 90° at blade tailing end region 66. The outlet angle of impeller blades 54 can be varied as shown in FIGS. 18A and 18B. In FIG. 18A, the downstream end or blade tailing region 66 of impeller blade 54 is shown with an outlet angle of 90° (i.e., the end region of the blade is perpendicular to the inner diameter of the pump housing or flow tube). In FIG. 18B, the end 66 of the impeller blade instead continues to curve past 90°. This embodiment can be advantageous for imparting the maximum pumping force on the blood. The preferred ranges for the entrance and outlet angles are given in Table 1 below.

Impeller blades 54 include axially longer impeller blades, such as longer blade 68, and axially shorter impeller blades, such as shorter blade 70. The alternate long and short blade arrangement on impeller 55 accommodates multiple magnetic poles for electric motor operation as discussed hereinafter, and still maintains adequate flow area through impeller 55. Presently, the preferred number of impeller blades is six, but a range from two to six blades provides permissible pump efficiency. If impeller 55 included six axially longer blades, such as longer blade 68, the flow area through impeller portion 50 is restricted to such an extent that the blades actually begin to block the flow they are intended to produce.

The junction between the inducer and the impeller can be defined as the point at which the angles of the long blades are about 17°.

Using the method of this invention, it was unexpectedly discovered that hemolysis does not necessarily increase with the number of blades, as anticipated. The alternating long-short blade arrangement of the six bladed impeller of the present invention does not cause hemolysis any more significantly than a two-bladed impeller. In some cases, an impeller with four long blades may cause more hemolysis than either a two or six bladed impeller. It is possible that the degree of hemolysis depends more on the number of long blades rather than the total number of blades.

Figure 4A:
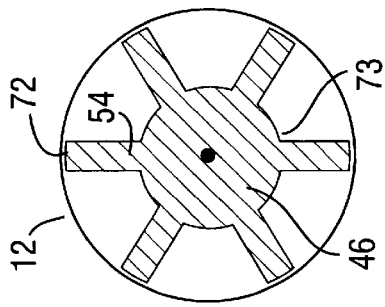
FIG. 4A is a cross-sectional view of a portion of an alternate impeller embodiment.
Figure 4:
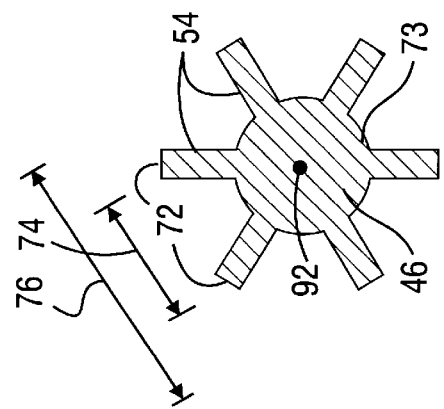
FIG. 4 is a cross-sectional view of a portion of an impeller showing non-radi-used blade tips.

FIG. 4 shows a portion of impeller 55 in cross-section to illustrate substantially flat, non-radiused blade tips 72. FIG. 4A shows an alternate embodiment of impeller 55 in cross-section. Blades 54 in this case have tips 72 that have curvature that is concentric with the inner wall of the pump housing or flow tube 12. The blade tips of FIG. 4A are the presently preferred embodiment.

Fully radiused blade tips are not preferred, because they allow too much blood to flow between the blade tip and the inner diameter of the flow tube, thus permitting undesirable blood recirculation patterns within the pump. Another disadvantage of fully radiused blade tips is that they require the magnets to be placed within the blades closer to the longitudinal axis of the rotor and further from the stator, which decreases efficiency.

FIG. 4 also illustrates a preferred rotor hub 73 with outside diameter 74 compared to the overall outside diameter 76 of inducer 53 and/or impeller 55. The preferred ratio is 0.48, although a range of 0.45 to 0.55 permits excellent pump operation. If the hub is smaller than permitted by this range, blood becomes excessively swirled and may tend to recirculate within pump 10 in the wrong flow direction to possibly damage the blood as well as reduce pump efficiency. If the hub is too large so as to be outside of this range, the hub tends to block flow through the pump 10.

The radial clearance 78 between inducer 53 and/or impeller 55 with respect to the pump housing inner wall 15 is preferably in the range shown below in Table 1. It was unexpectedly discovered that smaller radial clearances lower hemolysis. It was expected that smaller clearances would produce greater blood damage due to higher shear stresses on the blood.

In order to reduce the air gap between stator 80 and magnets 82, the magnets are preferably sealingly mounted within impeller blades 54. Reducing the air gap between the stator 80 and the magnets 82 increases motor efficiency, because magnetic flux is not as diffused as in motor designs with large air gaps. The preferred radial spacing or air gap between magnets 82 and stator 80 is from 0.01 inches to 0.035 inches. Magnets 82 are preferably rare earth magnets because of the higher magnetic flux produced by such magnets. Each magnet 82 is encapsulated in an individual pocket 84 to eliminate corrosion. Because magnets are individualized, motor torque and rotor weight can be easily adjusted in the manufacturing stage to provide motors that are tailored to the type of pump performance necessary without producing excessive pump weight.

Field winding 88 generates a magnetic field to rotate rotor 46. Stator 80 can be comprised of individual stator laminations 86 to eliminate eddy currents that generate heat and reduce efficiency. Alternatively, the stator can be made with no laminations. Heat flow from pump 10 is directed both into the blood stream and into the tissues surrounding pump 10. In this way, the blood is not heated in a manner that may damage the blood and, as well, the surrounding tissues do not have to absorb all the heat. Heat conductive flow paths using thermally conductive material, such as the metal of the stator or a thermally conductive gel, may be used to provide approximately the desired ratio of heat flow to the tissues compared to the heat flow to the blood.

Figure 2A:
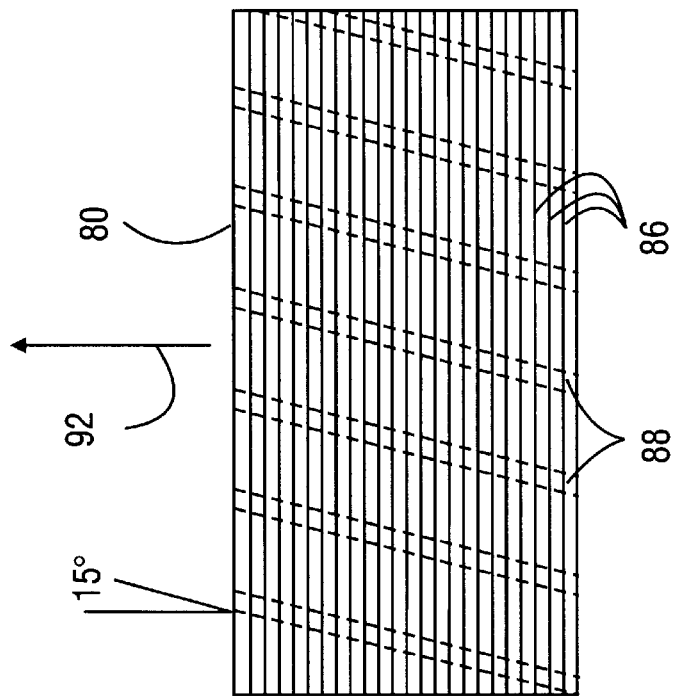
FIG. 2A is an elevational view indicating the skewed path of stator field windings through the stator.
Figure 2:
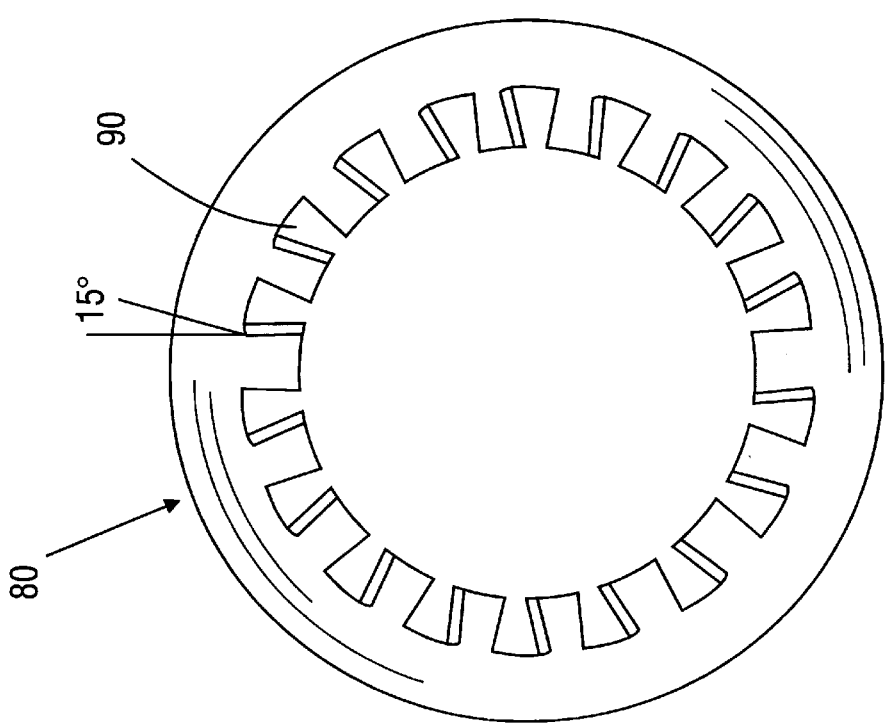
FIG. 2 is an end view of a stator showing stator laminations stacked to form a skewed stator.

In the embodiment illustrated in FIG. 2, stator 80, comprised of individual laminations 86, is stacked in a skewed manner such that pathways 90 provide a motor winding pathway that is offset from the rotor axis 92. The skew of laminations 86 may or may not correspond in some manner with the offset angle or changing offset angle of the row of magnets 82, and is not limited to the position shown in FIG. 2. A skewed stator 80 is also indicated in FIG. 2A, which shows an offset path from axis 92 for the field windings 88 which travel through stator 80. The skewing angle or offset from the rotor axis is used to optimize performance. The skewing angle of stator 80 may be variable rather than fixed along its length. However, the presently preferred embodiment does not employ this skewing.

An axial force is produced on rotor 46 during rotation, which can be varied by moving stator 80 axially along pump housing 12. Stator 80 is axially adjustable for this purpose, and could be fixed in position during manufacturing for optimal performance given the number of magnets to be used and given other factors discussed hereinafter. The axial force thus produced can be used to offset the thrust created during pumping to reduce the load on the front or rear bearing assemblies 24 and 42, respectively. The axial positioning of stator 80 may also be used to optimize electrical motor efficiency.

Figure 5:
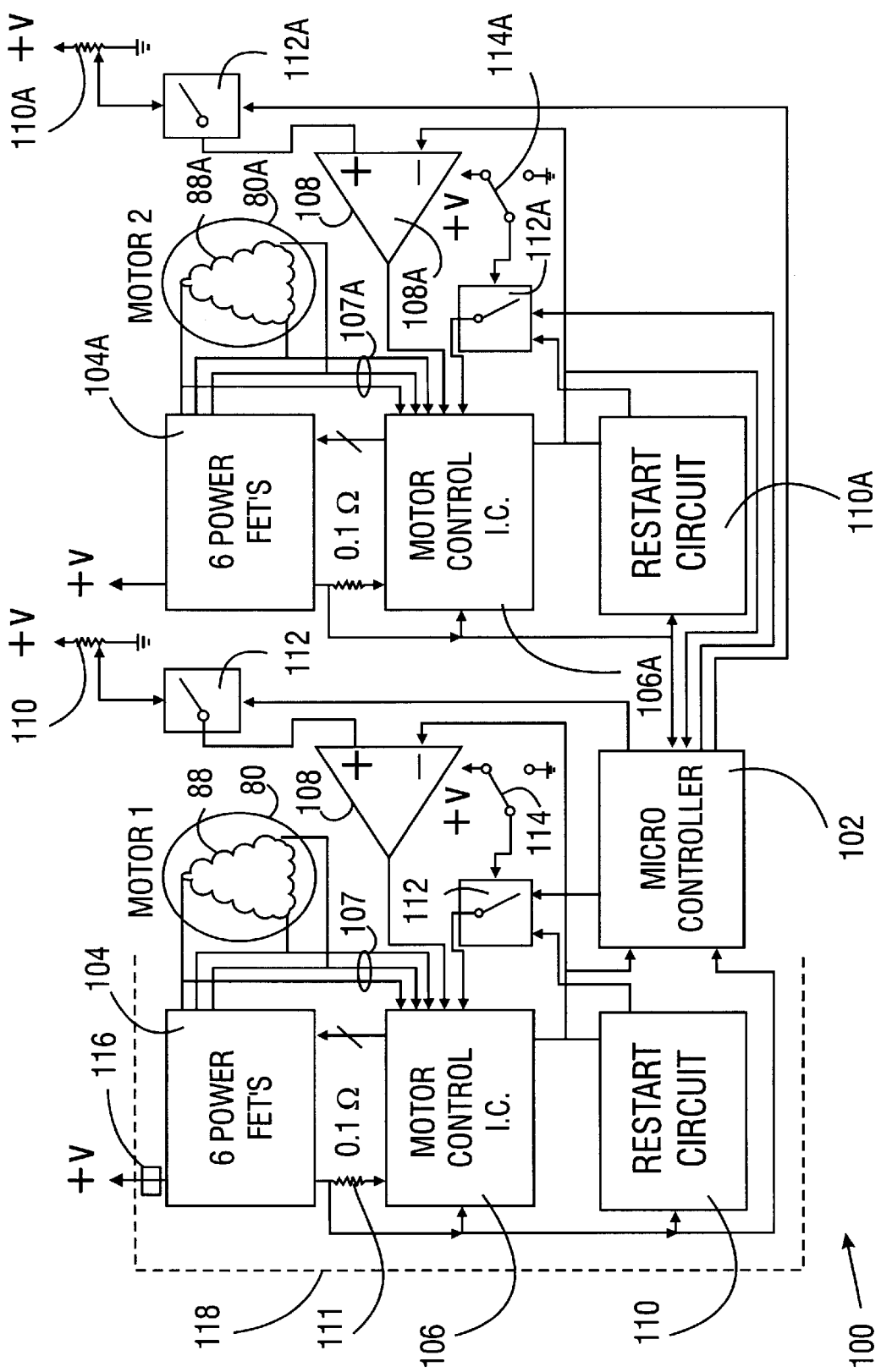
FIG. 5 is a block diagram of a control system including a back emf integrated circuit and a microprocessor.

Referring to FIG. 5, a block diagram of the control system 100 of the present invention is shown. Note that control system 100 may operate two motors 1 and 2. For some applications, either for implantation or for external use, it may be desirable to have two pumps connected either in parallel or in series. Thus, control system 100 can be easily configured for this purpose if desired. In addition, magnets (not shown) may be placed in the inducer hub to provide a secondary motor in the case of primary motor or controller failure. Various other back-up and redundancy configurations may be used. Micro-controller 102 may be programmed for pulsatile motor operation or continuous speed motor operation of one or more motors, as desired.

If only one pump is to be used, extra components may be removed. In FIG. 5, except for micro-controller 102, most components are duplicated to allow for operation of the two motors. For convenience, reference to corresponding components will be made to one number, with the corresponding component having an "a" suffix. Control system 100 operates either manually or by micro-control as discussed subsequently, and may be used for test purposes if desired.

Control system 100 applies current to stator windings 88. Preferably stator 80 includes three stator windings 88. Stator 80 generates a rotating magnetic field which magnets 82 and thus rotor 46 follow to produce motion. The motor stator may be three phase "Y" or "Delta" wound. The operation of the brushless D.C. motor of the present invention requires a proper sequence of power to be applied to stator windings 88. Two stator windings 88 have power applied to them at any one time. By sequencing the voltage on and off to the respective stator windings 88, a rotating magnetic field is produced.

A preferred embodiment three-phase motor requires a repetitive sequence of six states to generate a rotating magnetic field, although other commutation schemes could be used. The six states are produced by electronic commutation provided by power F.E.T.'s 104. If Motor 1 were sequenced through the six electrical states at a controlled frequency without feedback, its operation would be that of a stepper motor. In such a mode of operation, the motor rapidly loses its ability to generate torque as the rpm's increase.

Control system 100 detects back electromotive force or back emf to control motor operation. Whenever a conductor, such as field winding 88, is cut by moving magnetic lines of force, such as are generated by magnets 82, a voltage is induced. The voltage will increase with rotor speed. It is possible to sense this voltage in one of the three stator windings 88 because only two of the motor's windings are activated at any one time, to determine the rotor 46 position, and to activate commutator switches 104. The circuitry is much simpler and more reliable than Hall effect sensors which have been used in the past. Although a back emf control is the presently preferred embodiment, a Hall effect driven commutation scheme could also be used.

Back emf integrated circuit 106 provides sensors for detecting the back emf from lines indicated at 107, and operates commutation switches 104 accordingly. A presently preferred back emf integrated circuit includes a ML4411 motor controller integrated circuit. Each commutation switch F.E.T. is preferably turned all the way on or off for maximum power efficiency.

Back emf integrated circuit 106 also provides a start up mode operation when the back emf is not present or large enough for detection. From zero to approximately 200 rpm's, motor 1 operates in stepper motor fashion as described hereinbefore. Motor speed is controlled with a difference amplifier 108, which may take its speed signal from either micro-controller 102 or speed adjust pot 110 as selected by switch 112. A speed detection signal is available from the back emf integrated circuit 106 for this purpose.

Restart circuit 110 and micro-controller 102 monitor voltage developed across sense resistor 111 (present preference is about 0.1 ohms) and the frequency signal from back emf integrated circuit 106 to determine whether motor 1 should be restarted, i.e., due to a sudden increase or decrease in current or frequency. Switch 113 may be used to select between use of restart circuit 110, micro-controller 102, or a manual restart switch 114. Controller 102 may be programmed to produce an alarm signal if there are sudden changes in power consumption or frequency, as may occur if heart strength weakens or improves. To protect the electronics from electromagnetic interference (EMI), ferrite beads 116 are used with wires to an external power supply. The electronics are preferably hermetically sealed in case 118, which is formed of a high mu material to limit EMI.

The control system and its case 118 can suitably be located either inside the body of the patient or external to the body. The control system and pump can be supplied with power by batteries which likewise can be implanted in the patient's body, or kept in an external location. If the batteries are internal, they can suitably be recharged periodically transcutaneously (i.e., from a recharging unit that is placed on the patient's skin in close proximity to the implanted battery) or through a hard-wired recharging line that passes through the patient's skin.

To compare hemolysis results, an index of hemolysis (IH) is used. This is defined as the amount of hemoglobin liberated in grams per 100 liters of blood pumped against 100 mm Hg. In equation form:

$$IH = \Delta Hb \times V \times (1 - Ht) \times \frac{100}{(\text{Flow} \times \text{Time})}$$

where:
IH equals amount of hemoglobin liberated in grams per 100 liters of blood pumped against 100 mm Hg;
Ht is the hematocrit in decimal percent;
V is the blood volume in liters;
ΔHb is the amount of hemoglobin liberated in a fixed time period in grams/liter;

Flow is the flow rate in liters per minute; and

Time is the total time in minutes at that flow rate.

As to manufacturing and usage considerations, pump 10 is preferably manufactured using materials designed to be buoyant inside the body to make the completed pump neutrally buoyant or approximately neutrally buoyant. This minimizes stress on stitches or other means used to position the pump within the body. Thus, the rotor, rotor blades, and/or other components may be made with a lightweight material having sufficient thickness to produce a buoyant effect.

Pump 10 has numerous uses as a blood pump, including use as a portable blood pumping unit for field service. Pump 10 may also be used for other clinical applications involving other fluids. It could, for instance, be used in a compact heart-lung machine. Due to the small volume and size of pump 10, it can be placed close to a patient to minimize shock caused when initiating blood pump operation using a saline solution. Larger pumps, with larger volume, may be awkward to move close by a patient to eliminate this shock.

Thus, the blood pump of the present invention, particularly when optimized using the method of the present invention, has many advantages over the prior art. For instance, there are no blood seals which require bearing purge systems. No Hall Effect sensors are required which may tend to limit motor control reliability due to their complexity. As well, pump 10 provides low power consumption and very low levels of hemolysis.

Figure 6A:
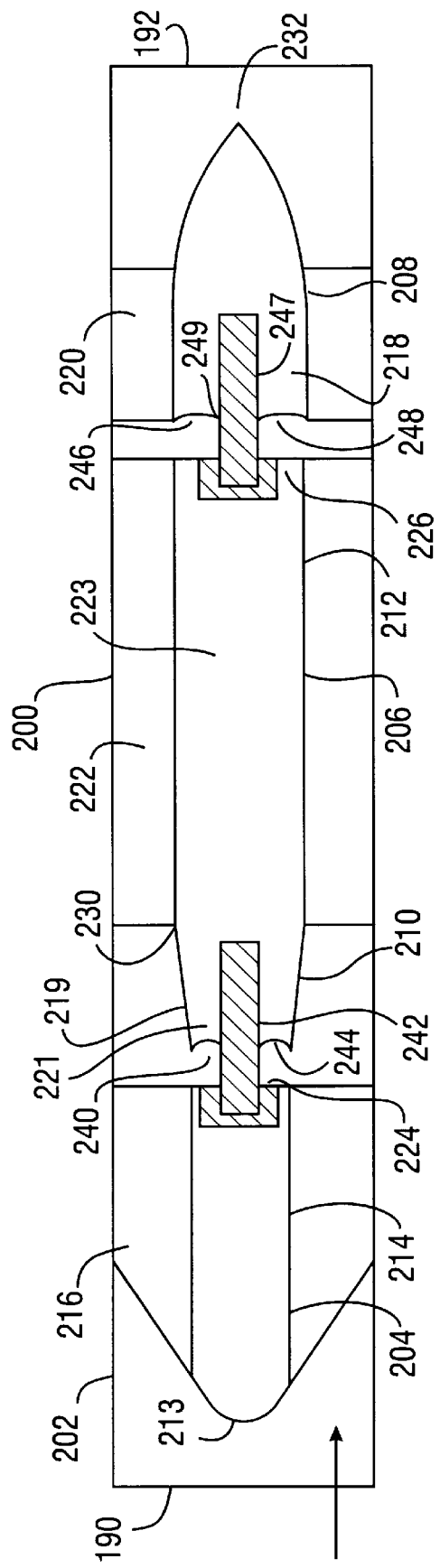
FIG. 6A is an elevational view, partly in section, of a rotary blood pump in accordance with the present invention, with blood flow generally from left to right.

FIG. 6A shows an improved blood pump 200, which comprises a flow tube that has an inner bore wall 202, a flow straightener 204, a rotor 206, and a diffuser 208. The blood flow in this figure is from left to right. The pump has an entrance (or upstream end) 190 and an exit (or downstream end) 192 at the two ends of the flow tube. The pump would also include a stator (not shown in FIG. 6A) generally similar to that shown in FIG. 1. As before, the rotor 206 comprises an inducer 210 and an impeller 212.

An embodiment of this blood pump suitable for implanting in an adult human would typically have an overall length of between about 2 and about 3 inches, and an inner diameter of the flow tube between about 0.37 inches and about 0.75 inches, preferably about 0.5 inches.

Flow straightener 204 comprises a flow straightener hub 214 and at least two flow straightener blades 216. The flow straightener hub 214 has a front tip 213 that is preferably parabolic in configuration. The flow straightener is secured to the inner bore wall 202 of the housing by an interference fit between the wall 202 and the outer tips of the flow straightener blades 216. This interference fit can be produced by heating the flow tube and chilling the flow straightener, inserting the flow straightener into the flow tube in the appropriate location, and then allowing them to reach a common temperature. Optionally, spot welds (not shown in FIG. 6A) can be made at the points of interference contact. Similarly, the diffuser 208 comprises a diffuser hub 218 and at least two diffuser blades 220. It has been found to be useful to have the diffuser blades have an inlet angle between about 25°–35°. The diffuser can be secured to the inner bore wall 202 of the housing by means of an interference fit between the wall 202 and the outer tips of the diffuser blades 220. Again, spot welds (not shown in FIG. 6A) may also be used at the points of contact.

The rotor 206 includes an inducer hub 221 and an impeller hub 223, and preferably has at least two blades 222, which can suitably be combined inducer and impeller blades. The rotor 206 is supported at each end by a front bearing assembly 224 and a rear bearing assembly 226. The upstream end of the inducer hub 221 preferably has an inducer extension portion 219 that does not have any blades on it. In a preferred embodiment, the rotor has a plurality of long blades, which constitute combined inducer and impeller blades, and a plurality of shorter blades located only on the impeller portion of the rotor. Each short blade is preferably located inbetween two long blades.

In the embodiment of FIG. 6A, the diameter of the various hubs in the device are not the same. There is a stepped differential between the flow straightener hub 214 and the inducer hub 221, and between the impeller hub 223 and the diffuser hub 218.

In particular, inducer hub 221 has a diameter greater at its upstream end than the diameter of the flow straightener hub 214 at its downstream end. If the inducer hub 221 has a diameter that varies along its length as shown in FIG. 6, then preferably the diameter at its upstream end is greater than that of the flow straightener hub, and the diameter of the rest of the inducer hub is still larger, gradually increasing along its axial length. (Downstream means closer to the exit 192 of the pump, and upstream means closer to the entrance 190 of the pump.) The diameter of the impeller hub 223 is preferably greater than the diameter of the inducer hub 221. Where the inducer hub has a tapered diameter as shown in FIG. 6A, the diameter at the downstream end of the inducer hub can be substantially the same as the diameter of the impeller hub, with a tapered or radiused transition 230 between the two, rather than a sharp transition.

Likewise, the diameter of the diffuser hub 218 at its upstream end is preferably greater than the diameter of the impeller hub 223. The diameter of the diffuser hub 218 is preferably gradually reduced toward its downstream end 232.

The inducer hub 221 has an upstream-facing end 240 in the center of which is inserted front shaft 242. The remainder of the upstream-facing end 240 has a dished face which can take the form of generally concave indentations 244. Similarly, diffuser hub 218 has an upstream-facing end 246 in the center of which is inserted rear shaft 247, and the remainder of the upstream-facing end 246 has a dished face which can take the form of generally concave indentations 248. Preferably the curved transition between the hub faces and the shafts is as smooth and gradual as possible, within manufacturing constraints. The concave indentations 244 and 248 help promote advantageous blood circulation patterns in the front gap between the flow straightener hub and the inducer hub, and in the rear gap between the impeller hub and the diffuser hub, thereby eliminating or minimizing undesirable thrombus formation in those gaps.

The front shaft 242 is fixedly attached in the inducer hub 221 and the rear shaft is fixedly attached in the diffuser hub 218 in FIG. 6A. However, it is presently preferred to have the rear shaft fixedly attached in the impeller hub, and the rear bearing located in the diffuser hub (i.e., a rear bearing assembly reversed from what is shown in FIG. 6A).

Preferred pump dimensions and parameters for the present invention are shown in Tables 1 and 2.

TABLE 1

| Parameter | flow-straightener | inducer | impeller | diffuser |
|---|---|---|---|---|
| entrance angle (°) | | | | |
| present preference | 0 | 10 | 17 | 28 |
| preferred range | — | 5–12 | 10–22 | 25–35 |

TABLE 1-continued

| Parameter | flow-straightener | inducer | impeller | diffuser |
|---|---|---|---|---|
| outlet angle (°) | | | | |
| present preference | 0 | 17 | 90 | 90 |
| preferred range | — | 12–20 | 90–110 | 80–110 |
| radial clearance (in) | | | | |
| present preference | — | 0.005 | 0.005 | — |
| preferred range | — | 0.002–0.008 | 0.002–0.008 | — |
| wrap (°) | | | | |
| present preference | — | 240 | — | 45 |
| preferred range | — | 180–360 | — | 30–90 |
| number of blades | | | | |
| present preference | 4 | 3 | 6 | 6 |
| preferred range | 2–5 | 2–4 | 2–6 | 4–7 |

TABLE 2

| Parameter | front gap | rear gap |
|---|---|---|
| axial clearance (in) | | |
| present preference | 0.052 | 0.050 |
| preferred range | 0.035–0.090 | 0.025–0.075 |

FIG. 6B shows an alternative embodiment in which the rotor 206, including both the inducer portion 210 and the impeller portion 212, has a constant diameter along its axial length. As in FIG. 6A, the diameter of the inducer hub 210 is greater than the diameter of the flow straightener hub 214, and the diameter of the diffuser hub 218 is greater at its upstream end than the diameter of the impeller hub 212. (The inducer and impeller blades are not shown in this figure.)

FIG. 6C shows another alternative embodiment. In this version, the diameters of the flow straightener hub 214, inducer hub 210, impeller hub 212, and diffuser hub 218 form a continuous axial profile or taper, with the usual gaps between the flow straightener hub 214 and the inducer hub 210, and between the impeller hub 212 and diffuser hub 218. (The inducer and impeller blades are not shown in this figure.) The flow straightener hub 214 continuously expands in diameter along its axial length from its front tip 213 to its downstream end, and the rotor hub 206 (comprising the inducer hub 210 and the impeller hub) continuously expands in diameter along its axial length. The diffuser hub 218 in this embodiment has a upstream portion 350 and a downstream portion 352 which are integral parts of the diffuser hub. The upstream portion has a continuously expanding diameter along its axial length, until it reaches apex 354 at which point the diameter begins to continuously reduce along the axial length toward the downstream tip 232 of the diffuser hub 218. In this embodiment, the angle of outward taper can suitably be 2–6°.

FIG. 7 shows the flow straightener 204, inducer 210, and front bearing assembly 224 of a slightly different embodiment in more detail. In this structure, the upstream-facing end 240 of the inducer hub 221, has a radiused taper or fillet 298 from the outer diameter 300 of the upstream edge of the inducer hub 221 to the front shaft 242. Optionally, the downstream-facing end 302 of the flow straightener hub 214 can similarly have a radiused taper or fillet 304. Similarly, as indicated in FIG. 6A, the upstream end of the diffuser hub 218 can include a radiused taper or fillet 249 to the rear shaft 247.

The front bearing assembly in FIG. 7 comprises a needle bearing 306. When a needle bearing is used in the front bearing assembly, the needle bearing interface 307 between the needle bearing pin 308 and the mating socket 309 is preferably located centrally in the front gap (i.e., approximately halfway between the downstream end of the flow straightener hub and the upstream end of the inducer hub.

FIG. 8 shows one advantage of the above-described configuration. As blood flows axially through the pump, some blood will recirculate in the front gap between the flow straightener hub 214 and the inducer hub 221. If the blood recirculation pattern in this gap is undesirable, blood clots will form in the gap. In order to prevent this, the structure around the gap is preferably configured to promote a single blood recirculation pattern 310, which will minimize or eliminate areas of blood stagnation in the gap. In particular, the use of radiused tapers 298 and 304 on each side of this gap, together with proper sizing of the gap, promote the single circular blood flow pattern 310. Absent this configuration, two or more blood circulation patterns will tend to form in the gap, resulting in lower blood recirculation velocity in certain regions of the gap, thus causing regions of stagnation and increased clot formation.

The inclusion of a curved upstream face 248 on the upstream-facing end 246 of the diffuser hub 218 as shown in FIG. 6A similarly promotes the formation of a single blood circulation pattern in the rear gap between the impeller hub 223 and the diffuser hub 218, again minimizing clot formation in that gap. In effect, the configuration of the ends of the hubs induces the blood flow in the pump to keep the gaps between the hubs washed out, so that clotting between the hubs will be minimized.

Figure 9:
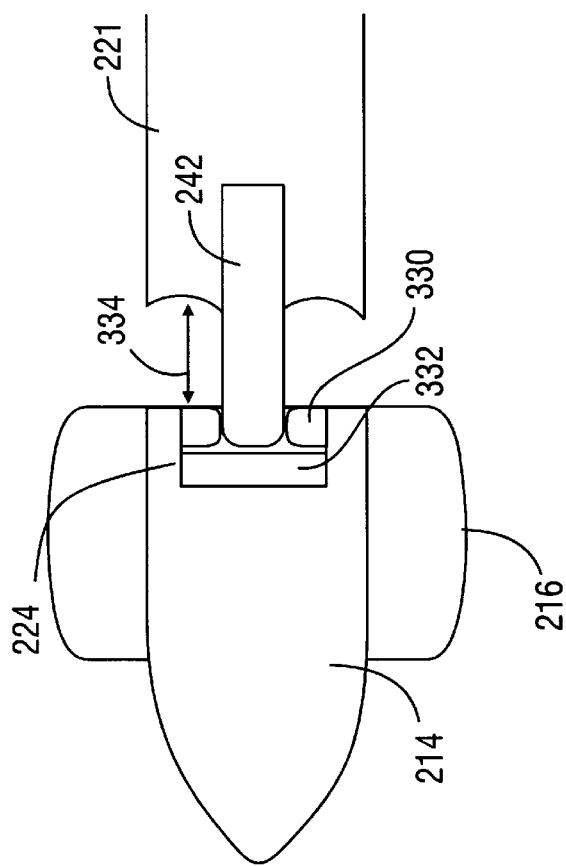
FIG. 9 is a partial elevational view, partly in section, of the upstream end of the internals of another embodiment of a rotary blood pump in accordance with the present invention.

Another version of front bearing assembly 224 is shown in more detail in FIG. 9. In this embodiment, front shaft 242 is fixedly secured in the inducer hub 221. The upstream end of front shaft 242 is supported by a bearing in the flow straightener hub 214 comprising an olive ring 330 and an endstone 332. Front shaft 242 rotates with the inducer hub 221, while the flow straightener hub 214, olive ring 330, and endstone 332 remain stationary. Alternatively, the front bearing assembly could be reversed, with the shaft mounted in the flow straightener hub, and the olive ring and endstone in the inducer hub. Although the upstream face of the inducer hub 221 in FIG. 9 tapers toward the shaft 242, it is depicted as having a sharp point of intersection with the shaft. In a presently preferred embodiment, the transition is smoother, i.e., the curved taper on the upstream face of the inducer hub gradually becomes as nearly tangent to the shaft as possible, within manufacturing constraints.

Figure 10B:
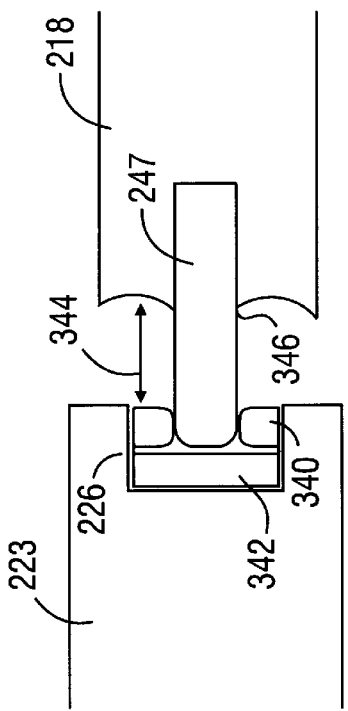
FIGS. 10A and 10B are elevational views in section of two alternate rear bearing assemblies for a blood pump in accordance with the present invention.
Figure 10A:
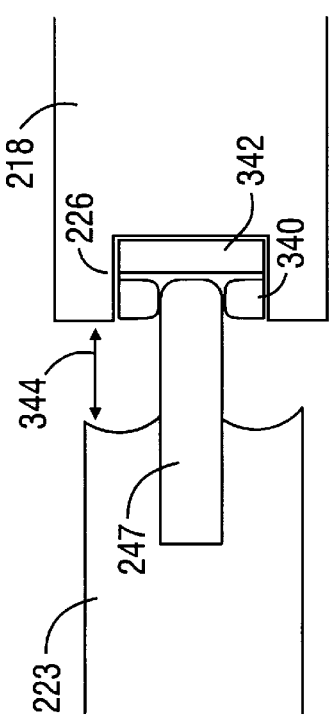

A preferred embodiment of the rear bearing assembly 226 is shown in FIG. 10A. In this embodiment, the rear shaft 247 is fixedly mounted in the impeller hub 223, and an olive ring 340 and endstone 342 are in the diffuser hub 218. In this embodiment, the rear shaft 247 rotates with the impeller hub.

An alternate embodiment of the rear bearing assembly 226, shown in FIG. 10B, includes a rear shaft 247 that is fixedly mounted in the diffuser hub 218, and an olive ring 340 and endstone 342 in the impeller hub 223. The rear shaft 247 does not rotate in this embodiment, instead remaining stationary with the diffuser hub 218. Impeller hub 223, olive ring 340, and endstone 342 rotate as part of the rotor.

The front gap 334 shown in FIG. 9 between the downstream end of flow straightener hub 214 and the upstream end of inducer hub 221 is preferably between about 0.05 and about 0.09 in. The rear gap 344 between the downstream end of impeller hub 223 and the upstream end of diffuser hub 218 is preferably between about 0.025 and about 0.075 inches. If these gaps are too small, blood will recirculate in the gaps at low velocities, leading to stagnation and clotting. If these gaps are too large, multiple blood recirculation patterns will occur in the gaps, leading to regions of stagnation and clotting.

The blood pump can be implanted in a patient who has a diseased heart in order to increase the rate of blood circulation. The manner in which the device is implanted will generally depend on the size of the patient and which of several pump embodiments is used. Suitable embodiments are show in FIGS. 11A–11D. In each of those figures, the blood flow direction is shown by arrow 368, the blood inlet is designated 376, the blood outlet is 378, the inner bore wall is 371, and the internal passageway for blood flow through the device is indicate by reference number 369. (The flow straightener, rotor, and diffuser are not shown in FIGS. 11A–11D.)

FIG. 11A shows an embodiment in which the pump's outer housing comprises a short, straight inlet housing segment 370. In this embodiment, the stator 373 is contained in stator housing segment 372, which forms a region of expanded diameter on the outside of the overall housing. On the downstream side of the stator housing segment 372 is the outlet housing segment 374, preferably having a diameter substantially the same as the inlet housing segment 370. The pump will typically be implanted with an inlet cannula. The inlet cannula can either be a separate tube that is connected to the inlet of the flow tube, or it can be an integral part of the inlet housing segment 370. The inlet cannula can be rigid or flexible, and can be attached to the inlet of the flow tube by, for example, a flexible vascular graft. When the embodiment of FIG. 11A is implanted, the inlet housing segment 370 will usually be inserted into the heart, with the stator housing segment 372 and the outlet housing segment 374 remaining outside the heart.

In the embodiment shown in FIG. 11A, although the inner diameter of the flow tube is constant, the thickness of the material forming the passageway 369 can vary. The housing can be thicker in the inlet housing segment 370 than in the region 375 underlying the stator housing segment 372, which can be termed the stator support region. It is important to keep the stator support region 375 thin because it is highly desirable to minimize the distance between the magnets on the rotor blades and the stator.

FIG. 11B shows an alternative embodiment in which the inlet housing segment 370 has an outer diameter equal to the outer diameter of the stator housing segment 372. In this embodiment, the outer diameter of the housing will typically be less than the outer diameter of the embodiment of FIG. 11A.

FIG. 11B also shows another variation, specifically that the inner diameter of the flow tube can be non-constant. In FIG. 11B, the inner diameter at the inlet end of the pump can be decreased toward the downstream end in order to create a venturi 377 in the inlet of the pump, while keeping the outer diameter relatively constant.

FIG. 11C shows another alternative embodiment, similar to that of FIG. 11A, but with a longer inlet housing segment 370 that in effect comprises an integral inlet cannula. This embodiment can be inserted into the heart as described above, but can alternatively be inserted at a point other than directly into the left ventricle. The longer inlet housing segment 370 permits this type of insertion, while permitting the inlet 376 to reach into the left ventricle.

FIG. 11D shows a similar embodiment, with the only difference being the use of a curved inlet housing segment 370. Again, the length of the inlet housing segment 370 permits the device to be inserted in the heart at a location other than the left ventricle, while permitting the inlet 376 of the pump to reach into the left ventricle.

The overall length of the pumps shown in FIGS. 11A and 11B will typically range from about 2–3.5 inches. In the embodiment having the extended inlet cannula as shown in FIG. 11C, the overall length of the pump will typically range from about 3–8 inches.

In general, the inlet housing segment, optionally with a separate inlet cannula, can be inserted through an incision in the wall of the heart, allowing the inlet of the pump to draw blood from the heart. A blood vessel graft can be attached to the outlet of the pump, and surgically connected to the aorta or another blood vessel, to carry blood on through the circulatory system.

Figure 12:
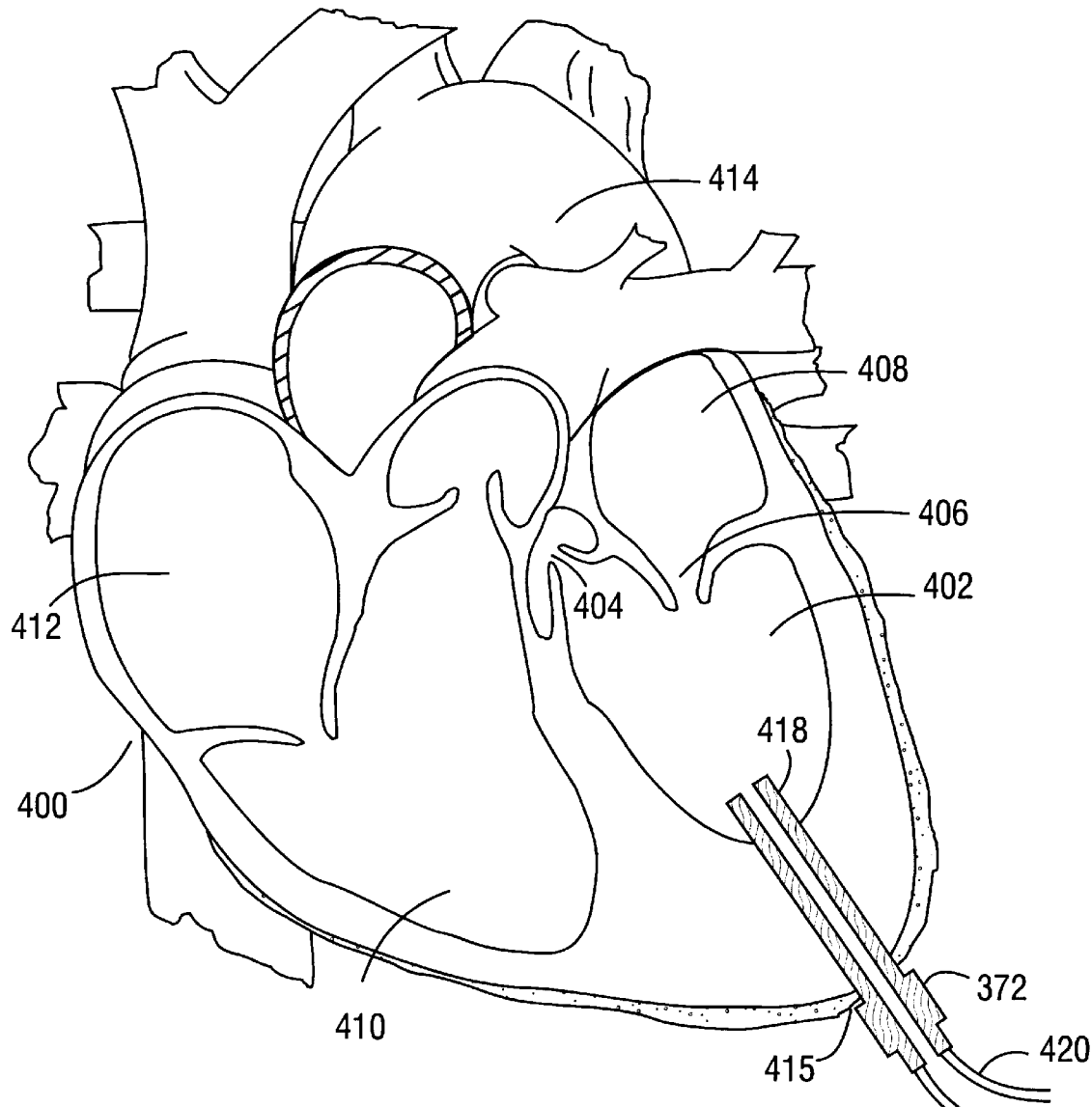
FIG. 12 is an elevational view in section of a human heart with a blood pump of the present invention implanted therein.

One specific means of implanting the pump of FIG. 11A in a patient's heart is shown in FIG. 12. The parts of the heart 400 shown include the left ventricle 402, the aortic valve 404, the mitral valve 406, the left atrium 408, the right ventricle 410, the right atrium 412, and the aorta 414. (The internals of the pump are not shown in this figure.) An incision is made in the wall of the heart, preferably at the apex 415 to permit the insertion of the inlet end 418 into the left ventricle 402. The stator housing 372 is preferably directly adjacent to the outside of the heart. The outlet of the pump is attached to a vascular graft 420, which is surgically connected to the aorta or another blood vessel, so that the blood that passes out of the pump can then be carried throughout the body.

In this implant configuration, the maximum length that the pump may extend outside the heart is about 6 cm, in order for it to fit between the heart and diaphragm of a typical adult.

The contractions of the heart will tend to expel the pump, so it is necessary to firmly attached it to the heart in some fashion. There are several alternative ways this can be done. One way is shown in FIG. 13. In this embodiment, again using a pump like that shown in FIG. 11A, the pump 416 comprises a short, straight inlet end 418, and the stator housing 450 has a larger outer diameter than the inlet end. The inlet end 418 of the pump 416 is inserted into the incision in the heart wall until the stator housing 450 is directly adjacent to the exterior 452 of the heart wall. (The bottom half of the pump is not shown in this figure; the longitudinal axis of the pump 416 is indicated by dotted line 454.)

Two sewing rings 460 and 462 are used to fasten the pump to the heart. These sewing rings are O-shaped and encircle the incision and the pump housing. The first sewing ring 460 is connected to the tissue of the heart wall 452 by sutures 464. A washer-like extension 470 on the housing 450 is located between the two sewing rings 460 and 462. The second sewing ring 462 is fixedly attached to the housing of the pump 416. This can be done by means of a wire 463 within the sewing ring 462 that can be drawn tight to hold the sewing ring 462 firmly against the pump housing. The two sewing rings are then connected to each other by sutures 466, thus firmly connecting the implanted pump 416 to the heart and preventing the pump from being expelled when the left ventricle contracts.

An alternative embodiment is shown in FIG. 14. The outer sewing ring 462, instead of being located on the outer diameter of the stator housing 450, is located in front of the stator housing 450 (i.e., toward the inlet end of the pump relative to the stator). A washer-like extension 470 on the pump housing is disposed between the two sewing rings 460 and 462. The first sewing ring 460 is attached to the exterior of the heart 452 with sutures 464, and the two sewing rings 460 and 462 are attached to each other with sutures 466. The sewing ring 462 is secured to the housing by means of a wire as described above.

The embodiments shown in FIGS. 13 and 14 have the advantage of requiring a relatively small incision in the heart wall, but they have the disadvantage of extending the pump for a distance of several cm outside the heart. In some patients it would be more desirable to reduce the distance the pump extends outside the heart. One way to achieve this is shown in FIG. 15. In this embodiment, using the pump housing configuration of FIG. 11B, the housing of the pump 416 is large enough in diameter to contain the stator without any bulge on the outer diameter of the housing. This configuration permits the pump 416, including the stator, to be inserted entirely or nearly entirely into the left ventricle, with only the outlet end 474 of the flow tube outside the wall of the heart. Sewing rings 460 and 462, washer-like extension 470, wire 463, and sutures 464 and 466 are as described above. A vascular graft (not shown) is attached to outlet 474 as described above. This embodiment has the advantage of requiring less space outside the heart for the pump, but requires a bigger hole in the wall of the heart.

Figure 16:
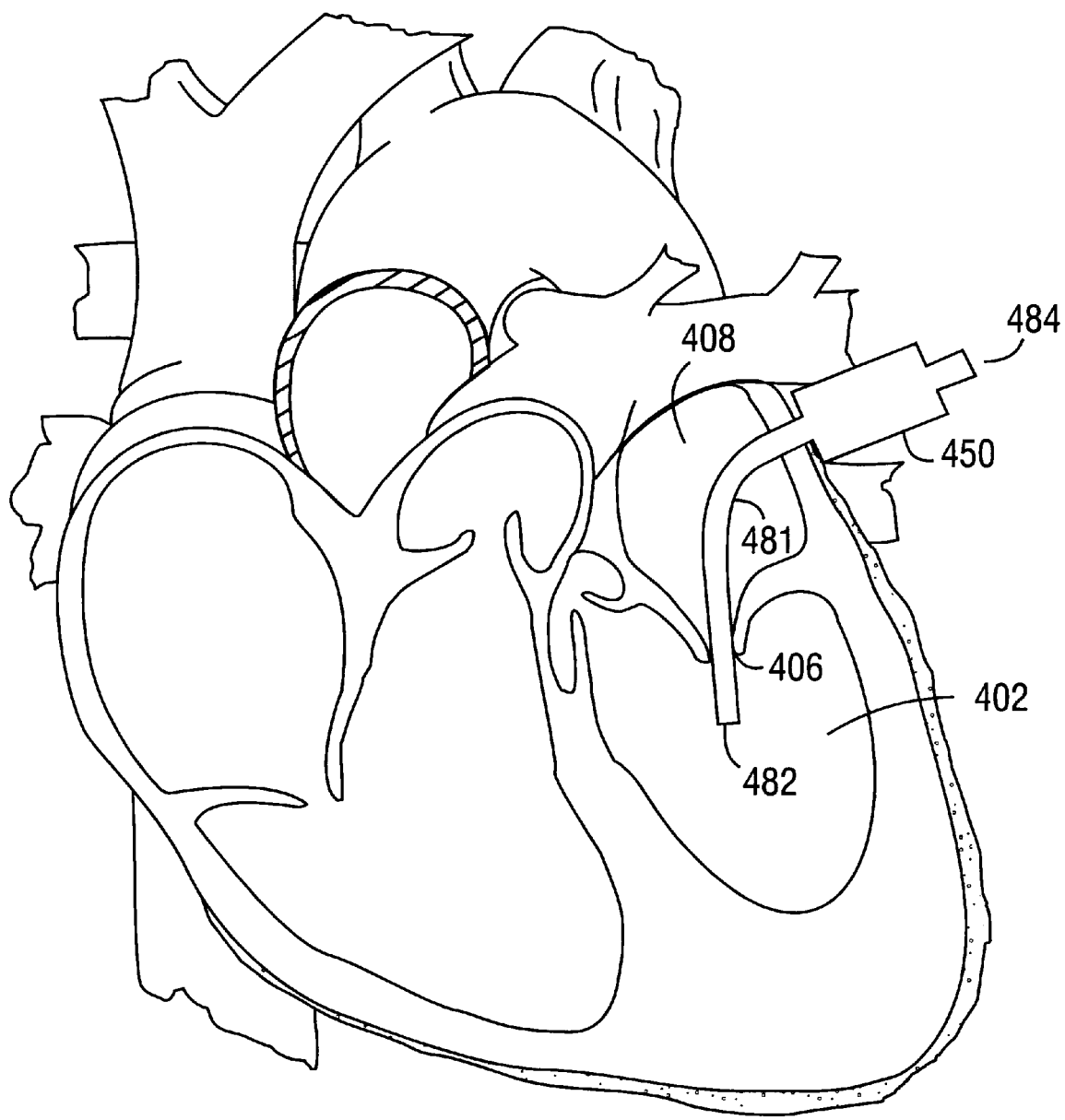
FIG. 16 is an elevational view in section of a human heart with another embodiment of a blood pump of the present invention implanted therein.

Some patients needing a ventricle assist device may have hearts that are too small to readily permit the implant configurations shown in FIGS. 12–15. In such cases, it may be desirable to use the pump of FIG. 11D and insert the pump into the heart at a different point. In the particular configuration shown in FIG. 16, the pump has a curved inlet 481 that is inserted through an incision in the wall of the heart into the left atrium 408, down through the mitral valve 406, and into the left ventricle 402. The portion of the housing containing the stator 450 and the outlet 484 are outside the heart in this configuration. In this way, the inlet 482 of the pump is located in the left ventricle as in the other embodiments, and the outlet 484 of the pump can deliver blood, via an outflow graft (not shown), to the rest of the body.

Alternatively, the inlet cannula could be straight as shown in FIG. 11C, but still inserted through the left atrium and mitral valve down into the left ventricle. In the configurations of FIGS. 11C and 11D, the inlet cannula optionally can be flexible.

Figure 17:
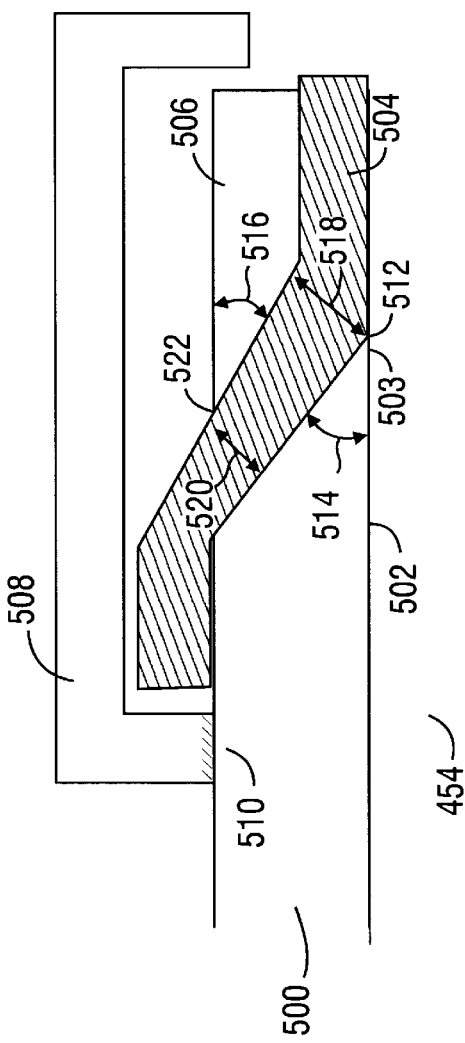
FIG. 17 is an elevational view in section of the outlet end of a blood pump in accordance with the present invention.

One embodiment of the connection between the outflow graft and the pump housing is shown in FIG. 17. The outlet end 500 of the pump housing is shown. (Only one half is shown in FIG. 17; the other half would be located on the other side of longitudinal axis 454.) The outlet end of the pump housing has a tapered end 502. An outflow graft 504 overlaps with the tapered end 502 of the housing. A first retaining member, for example a ring 506 having a wedge-shaped cross-section, is located around the end of the graft 504; i.e., the end of the graft is compressed between the ring 506 and the tapered end 502 of the housing. A second retaining member, for example a ring 50, is located around this assembly to hold the ring 506 and graft 504 in place relative to the pump housing. The ring 508 can be attached to the housing 502 by threads 510.

The ring 506 and the tapered end 502 of the housing preferably have different angles of taper. The housing has a taper of a first angle 514, and the tapered end of the ring 506 has a second angle 516. First angle 514 is preferably greater than second angle 516. As a result, the distance between the tapered end 502 of the housing and the ring 506 will not be constant. At the extreme downstream end of the housing, there will be a gap equal to a first distance 518, and further upstream, at the tapered end 522 of the ring 506, the gap will be equal to a second distance 520. The first distance will be greater than the second distance 520.

The effect of this differential will be to compress the outflow graft 504 the most at the end 522 of the ring 506, and compress it less at the extreme downstream end 503 of the housing. An advantage of this configuration is that it provides secure holding of the outflow graft relative to the pump housing, and also provides a smooth interface 512 on the inner diameter of the pump housing between the pump housing itself and the outflow graft. In other words, the blood flowing out of the pump experiences a smooth profile transition between the pump and the graft, instead of an abrupt change in diameter.

Suitable materials for the structure shown and described above are known to persons skilled in this field, and would include a variety of biocompatible materials that are used in other implantable devices. Suitable examples would include titanium for the housing and the inlet and outlet cannulas, as well as the flow straightener, rotor, and diffuser, including both the hubs and the blades thereon. Dacron is another suitable material that can be used for some parts of the device. The sewing rings can be, for example, a silicone ring wrapped with Dacron.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A blood pump, comprising:

a pump housing comprising a flow tube having a blood flow path therethrough, a blood inlet, and a blood outlet;

a stator attached to the pump housing, the stator having a stator field winding for producing a stator magnetic field;

a rotor located within the flow tube for rotation in response to the stator magnetic field, the rotor comprising an inducer and an impeller;

the inducer comprising an inducer hub and at least one inducer blade attached to the inducer hub;

the impeller being located downstream of the inducer, and comprising an impeller hub and at least one impeller blade attached to the impeller hub; and a diffuser located within the flow tube downstream of the impeller, and comprising a diffuser hub and at least one diffuser blade attached to the diffuser hub;

where the diffuser hub has an upstream end and the impeller hub has a downstream end, and the upstream end of the diffuser hub has a diameter greater than the diameter of the downstream end of the impeller hub.

2. The blood pump of claim 1, where there is an axial gap between the downstream end of the impeller hub and the upstream end of the diffuser hub, and the size of that gap induces a single blood recirculation flow pattern in the gap.

3. The blood pump of claim 1, where the impeller hub is axially spaced from the diffuser hub by between about 0.025 and about 0.075 inches.

4. The blood pump of claim 1, where the diffuser is secured to the flow tube.

5. The blood pump of claim 1, further comprising a flow straightener located within the flow tube, upstream of the inducer, and comprising a flow straightener hub and at least one flow straightener blade attached to the flow straightener hub.

6. The blood pump of claim 5, where there is an axial gap between the downstream end of the flow straightener hub and the upstream end of the inducer hub, and the size of that gap induces a single blood recirculation flow pattern in the gap.

7. The blood pump of claim 5, where the inducer hub has an upstream end and the flow straightener hub has a downstream end, and the upstream end of the inducer hub has a diameter greater than the diameter of the downstream end of the flow straightener hub.

8. The blood pump of claim 5, where the flow straightener is secured to the flow tube.

9. The blood pump of claim 5, further comprising a front bearing assembly which comprises a front shaft and a bearing, with one of the front shaft and bearing being attached to the upstream end of the inducer hub, and the other being attached to the downstream end of the flow straightener hub.

10. The blood pump of claim 9, where the front shaft is attached to the upstream end of the inducer hub, and further comprising a curved transition between the upstream end of the inducer hub and the front shaft.

11. The blood pump of claim 5, where the flow straightener hub is axially spaced from the inducer hub by between about 0.05 and about 0.09 inches.

12. The blood pump of claim 5, where the flow straightener, the inducer, the impeller, and the diffuser all have a common longitudinal axis.

13. The blood pump of claim 5, where the diameter of the flow straightener hub, inducer hub, and the impeller hub each increase from their upstream end to their downstream end.

14. The blood pump of claim 1, further comprising a rear bearing assembly which comprises a rear shaft and a bearing, with one of the rear shaft and bearing being attached to the downstream end of the impeller hub, and the other being attached to the upstream end of the diffuser hub.

15. The blood pump of claim 14, where the rear shaft is attached to the downstream end of the impeller hub, and further comprising a curved transition between the downstream end of the impeller hub and the rear shaft.

16. The blood pump of claim 1, further comprising an inducer hub extension on the upstream end of the inducer, the inducer hub extension having no inducer blades on it.

17. The blood pump of claim 1, where the inducer, the impeller, and the diffuser all have a common longitudinal axis.

18. The blood pump of claim 1, where the diameter of the inducer hub increases from its upstream end to its downstream end.

19. The blood pump of claim 1, where the impeller hub has a diameter no less than the diameter of the inducer hub.

20. The blood pump of claim 1, where the diffuser hub comprises an upstream segment and a downstream segment, both segments being integral parts of the diffuser hub, and an apex at the outer diameter of the diffuser hub at the point where the upstream segment meets the downstream segment; where the diameter of upstream segment increases from its upstream end to the apex, and where the diameter of the downstream segment decreases from the apex to its downstream end.

21. The blood pump of claim 1, where each diffuser blade has an inlet angle between about 25°–35°.

22. The blood pump of claim 1, further comprising at least one interconnecting blade segment which interconnects at least one inducer blade and at least one impeller blade to form a single continuous blade through the inducer and the impeller of the rotor.

23. The blood pump of claim 1, further comprising at least one magnet attached to at least one inducer blade or impeller blade.

24. The blood pump of claim 1, further comprising a plurality of magnets connected to at least one inducer blade or impeller blade.

25. The blood pump of claim 1, where the pump housing has an outer surface that comprises an inlet housing segment, a stator housing segment, and an outlet housing segment.

26. The blood pump of claim 25, where the stator housing segment has a larger outer diameter than the inlet housing segment and the outlet housing segment.

27. The blood pump of claim 25, where the inlet housing segment and the stator housing segment having substantially the same outer diameter, and the outlet housing segment has a smaller outer diameter.

28. The blood pump of claim 25, where the inlet housing segment is straight.

29. The blood pump of claim 25, where the inlet housing segment is curved.

30. The blood pump of claim 25, where the downstream end of the outlet housing segment has a tapered thickness, with the thickness being a minimum at the outlet end of the housing.

31. A blood pump, comprising:
  a pump housing comprising a flow tube having a blood flow path therethrough, a blood inlet, and a blood outlet;
  a stator secured to the pump housing, the stator having a stator field winding for producing a stator magnetic field;
  a flow straightener that is located within the flow tube and is secured to the flow tube, and comprising a flow straightener hub and at least one flow straightener blade attached to the flow straightener hub;
  a rotor located within the flow tube for rotation in response to the stator magnetic field, the rotor comprising an inducer and an impeller;
  the inducer being located downstream of the flow straightener, and comprising an inducer hub and at least one inducer blade attached to the inducer hub;
  the impeller being located downstream of the inducer, and comprising an impeller hub and at least one impeller blade attached to the impeller hub;
  a diffuser that is located within the flow tube downstream of the impeller and is secured to the flow tube, and comprising a diffuser hub and at least one diffuser blade attached to the diffuser hub;
  a front bearing assembly which comprises a front shaft that is attached to the inducer hub, and a bearing supporting one end of the front shaft, the bearing being mounted on the downstream end of the flow straightener hub;
  a curved transition between the upstream end of the inducer hub and the front shaft;
  a rear bearing assembly which comprises a rear shaft that is attached to the downstream end of the impeller hub, and a bearing supporting one end of the rear shaft, the bearing being mounted on the upstream end of the diffuser hub; and
  a curved transition between the downstream end of the impeller hub and the rear shaft;
  where the upstream end of the inducer hub has a diameter greater than the diameter of the downstream end of the flow straightener hub; and where there is an axial gap between the downstream end of the flow straightener hub and the upstream end of the inducer hub, and the size of that gap induces a single blood recirculation flow pattern in the gap.

32. A blood pump implant assembly, comprising:

a pump housing comprising a flow tube having a blood flow path therethrough, a blood inlet, and a blood outlet;

a stator attached to the pump housing, the stator having a stator field winding for producing a stator magnetic field;

a rotor located within the flow tube for rotation in response to the stator magnetic field, the rotor comprising an inducer and an impeller;

the inducer comprising an inducer hub and at least one inducer blade attached to the inducer hub; and the impeller being located downstream of the inducer, and comprising an impeller hub and at least one impeller blade attached to the impeller hub;

a diffuser located within the flow tube downstream of the impeller, and comprising a diffuser hub and at least one diffuser blade attached to the diffuser hub; and at least one sewing ring which is attached to the housing of the blood pump;

where the diffuser hub has an upstream end and the impeller hub has a downstream end, and the upstream end of the diffuser hub has a diameter greater than the diameter of the impeller hub at its downstream end.

33. The implant assembly of claim 32, further comprising a flow straightener located within the flow tube, upstream of the inducer, and comprising a flow straightener hub and at least one flow straightener blade attached to the flow straightener hub.

34. The implant assembly of claim 33, where the inducer hub has an upstream end and the flow straightener hub has a downstream end, and the upstream end of the inducer hub has a diameter greater than the diameter of the downstream end of the flow straightener hub.

35. The implant assembly of claim 32, where the blood pump housing has an outer surface that comprises an inlet housing segment, a stator housing segment, and an outlet housing segment.

36. The implant assembly of claim 35, where the inlet housing segment is curved.

37. The implant assembly of claim 35, where the inlet housing segment is attached to a curved inlet cannula.

38. The implant assembly of claim 35, where the inlet housing segment is attached to a flexible inlet cannula.

39. The implant assembly of claim 35, where the inlet housing segment is straight.

* * * * *